United States Patent
Otsu et al.

(10) Patent No.: US 8,247,089 B2
(45) Date of Patent: Aug. 21, 2012

(54) ORGANIC ELECTROLUMINESCENCE ELEMENT MATERIAL, ORGANIC ELECTROLUMINESCENCE ELEMENT, DISPLAY DEVICE AND LIGHTING APPARATUS

(75) Inventors: Shinya Otsu, Tokyo (JP); Eisaku Katoh, Tokyo (JP)

(73) Assignee: Konica Minolta Holdings, Inc., Tokyo (JP)

( * ) Notice: Subject to any disclaimer, the term of this patent is extended or adjusted under 35 U.S.C. 154(b) by 830 days.

(21) Appl. No.: 12/297,318

(22) PCT Filed: Apr. 13, 2007

(86) PCT No.: PCT/JP2007/058156
§ 371 (c)(1),
(2), (4) Date: Oct. 16, 2008

(87) PCT Pub. No.: WO2007/119816
PCT Pub. Date: Oct. 25, 2007

(65) Prior Publication Data
US 2009/0302745 A1    Dec. 10, 2009

(30) Foreign Application Priority Data
Apr. 19, 2006 (JP) ................................. 2006-115411

(51) Int. Cl.
*H01L 51/54* (2006.01)
*C09K 11/00* (2006.01)

(52) U.S. Cl. ........ 428/690; 428/917; 313/504; 313/506; 252/301.16; 252/301.32; 257/40; 257/103; 257/E51.051; 549/43; 549/460

(58) Field of Classification Search .................. None
See application file for complete search history.

(56) References Cited

U.S. PATENT DOCUMENTS

| | | | | | |
|---|---|---|---|---|---|
| 4,551,404 | A | * | 11/1985 | Hiro et al. | 430/58.4 |
| 2002/0079835 | A1 | * | 6/2002 | Lee | 313/506 |
| 2002/0086180 | A1 | * | 7/2002 | Seo et al. | 428/690 |
| 2004/0076853 | A1 | | 4/2004 | Jarikov | |
| 2004/0110031 | A1 | * | 6/2004 | Fukuda et al. | 428/690 |
| 2006/0251923 | A1 | * | 11/2006 | Lin et al. | 428/690 |
| 2007/0104976 | A1 | * | 5/2007 | Iwakuma et al. | 428/690 |

FOREIGN PATENT DOCUMENTS

| | | | |
|---|---|---|---|
| JP | 2002-308837 | | 10/2002 |
| JP | 2003-286260 | | 10/2003 |
| JP | 2004-300044 | A * | 10/2004 |
| JP | 2004-311404 | | 11/2004 |
| JP | 2005-112765 | A * | 4/2005 |
| JP | 2005-314239 | | 11/2005 |
| JP | 2006028176 | | 2/2006 |
| JP | 2006049570 | | 2/2006 |
| JP | 2006069964 | | 3/2006 |
| WO | 01/72927 A1 | | 10/2001 |
| WO | WO 2005/057987 A1 | * | 6/2005 |
| WO | 2006/128800 A1 | | 12/2006 |

OTHER PUBLICATIONS

English machine translation of JP 2004-300044 A, 2004.*
English machine translation of JP 2005-112765 A, 2005.*
Steven L Murov, et al. Handbook of Photochemistry, Second Edition, Revised and Expanded, 1993, Marcel Dekker, Inc.

* cited by examiner

*Primary Examiner* — Jennifer Chriss
*Assistant Examiner* — Michael H Wilson
(74) *Attorney, Agent, or Firm* — Lucas & Mercanti, LLP

(57) ABSTRACT

Provided is an organic EL element, which has a controlled emission wavelength, a high emission efficiency and a long emission life. An organic EL element material for such organic EL element, a lighting device, and a display device using such organic EL element are also provided.

20 Claims, 1 Drawing Sheet

LIGHT

LIGHT

ORGANIC ELECTROLUMINESCENCE ELEMENT MATERIAL, ORGANIC ELECTROLUMINESCENCE ELEMENT, DISPLAY DEVICE AND LIGHTING APPARATUS

This is a U.S. National Phase Application under 35 U.S.C. 371 of International Application PCT/JP2007/058156, filed on Apr. 13, 2007, which claims the priority of Japanese Application No. 2006-115411, filed Apr. 19, 2006, the entire content of both Applications are hereby incorporated by reference.

TECHNOLOGY FIELD

The present invention relates to an organic electroluminescence element material, an organic electroluminescence element, a display device and a lighting apparatus.

BACKGROUND OF ART

Conventionally, an emission type electronic display device includes an electroluminescence display (hereinafter, referred to as an ELD). A constituent element of ELD includes such as an inorganic electroluminescent element and an organic electroluminescent element (hereinafter, referred to as an organic EL element). An inorganic electroluminescent element has been utilized as a flat light source, however, requires a high voltage of alternating current to operate an emission element.

On the other hand, an organic electroluminescent element is an element provided with a constitution comprising an emission layer containing a emitting substance being sandwiched with a cathode and an anode, and an exciton is generated by an electron and a positive hole being injected into the emission layer to be recombined, resulting emission utilizing light release (fluorescence-phosphorescence) at the time of deactivation of said exciton; the emission is possible at a voltage of approximately a few to a few tens volts, and an organic electroluminescent element is attracting attention with respect to such as superior viewing angle and high visual recognition due to a self-emission type as well as space saving and portability due to a completely solid element of a thin layer type.

In an organic electroluminescence in view of the future practical application, desired has been development of an organic EL element which efficiently emits at a high luminance with a low electric consumption. Examples of such technologies are a slight amount of a fluorescent substance doped in a stilbene derivative, distyrylarylene derivative or a tristyrylarylene derivative, to achieve improved emission luminance and a prolonged lifetime of an element (for example, refer to Patent Document No. 1). Further, there are known such as an element having an organic emission layer comprising a 8-hydroxyquinoline aluminum complex as a host compound which is doped with a slight amount of a fluorescent substance (for example, refer to Unexamined Japanese Patent Application Publication (hereinafter referred to as JP-A) No. 63-264692) and an element having an organic emission layer comprising a 8-hydroxyquinoline aluminum complex as a host compound which is doped with quinacridone type dye (for example, refer to JP-A No. 3-255190).

Regarding to the technologies disclosed in the above-described Patent Documents, when emission from an excited singlet is utilized, since a generation ratio of a singlet exciton to a triplet exciton is 1/3, that is, a generation probability of an emitting exciton species is 25% and a light taking out efficiency is approximately 20%, the limit of a quantum efficiency ($\eta$ext) of taking out is said to be 5%.

However, since an organic EL element which utilizes phosphorescence from an excited triplet has been reported from Princeton University (M. A. Baldo et al., Nature vol. 395, pp. 151-154 (1998)), researches on materials exhibiting phosphorescence at room temperature have come to be active. For example, it is also disclosed in A. Baldo et al., Nature, vol. 403, No. 17, pp. 750-753 (2000), and U.S. Pat. No. 6,097,147.

Since the upper limit of internal quantum efficiency becomes 100% by utilization of an excited triplet, which is principally 4 times of the case of an excited singlet, it may be possible to achieve almost the same ability as a cooled cathode ray tube to attract attention also for an illumination application.

For example, in such as S. Lamansky et al., J. Am. Chem. Soc., vol. 123, p. 4304 (2001), many compounds mainly belonging to heavy metal complexes such as iridium complexes have been synthesized and studied. Further, in aforesaid, A. Baldo et al., Nature, vol. 403, No. 17, pp. 750-753 (2000), utilization of tris(2-phenylpyridine)iridium as a dopant has been studied.

In addition to these, M. E. Tompson et al., at The 10th International Workshops on Inorganic and Organic Electroluminescence (EL'00, Hamamatsu), have studied to utilize $L_2Ir$ (acac) such as $(ppy)_2Ir(acac)$ as a dopant, Moon-Jae Youn. Og., Tetsuo Tsutsui et al., also at The 10th International Workshops on Inorganic and Organic Electroluminescence (EL'00, Hamamatsu), have studied utilization of such as tris(2-(p-tolyl)pyridine)iridium $(Ir(ptpy)_3)$ and tris(benzo[h]quinoline)iridium $(Ir(bzq)_3)$ (herein, these metal complexes are generally referred to as orthometalated iridium complexes.).

Further, in also the aforesaid, S. Lamansky et al., J. Am. Chem. Soc., vol. 123, p. 4304 (2001), studies have been carried out to prepare an element utilizing various types of iridium complexes.

An orthometalated complex provided with platinum instead of iridium as a center metal is also attracting attention. With respect to these types of complexes, many examples having a characteristic ligand are known (for example, refer to JP-A 2002-332291, JP-A 2002-332292, JP-A 2002-338588, JP-A 2002-226495, and JP-A 2002-234894).

AS a host compound of the phosphorescent light-emitting dopants, carbazole derivatives represented by CBP and m-CP have been well known. Though m-CP and their derivatives have been known as a blue light emitting host compound, emission efficiency and light emission life have not reached a sufficiently satisfied level (for example, refer to Patent Documents 1 and 2).

Patent Document 1: International Publication Pamphlet 2003/80760
Patent Document 2: International Publication Pamphlet 2004/74399

DISCLOSURE OF THE INVENTION

Issues to be Solved by the Invention

The present invention was achieved in consideration of the above issues, and it is an object of the present invention to provide an organic EL element exhibiting controlled light emission wavelength, high light emission efficiency and long light emission life, an organic EL element material for use thereof, and a lighting apparatus and a display device both of which employ the aforesaid organic EL element.

The above issues of the present invention have been achieved by the following constitutions.

Item 1. An organic electroluminescence element material, wherein the organic electroluminescence element material is represented by Formula (1) below.

Formula (1):

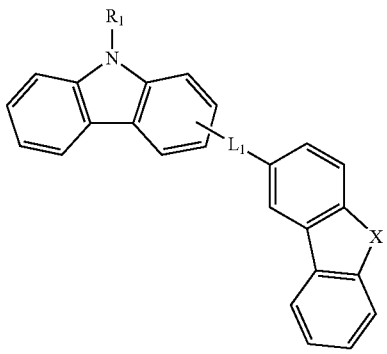

(wherein $R_1$ represents a hydrogen atoms an aliphatic group, an aromatic hydrocarbon cyclic group, or a heterocyclic group; $L_1$ represents a linking group or a simple bond; X represents O or S; and the compound represented by Formula (1) may have a substituent at other position.)

Item 2. An organic electroluminescence element material, wherein the organic electroluminescence element material is represented by Formula (2) below.

Formula (2):

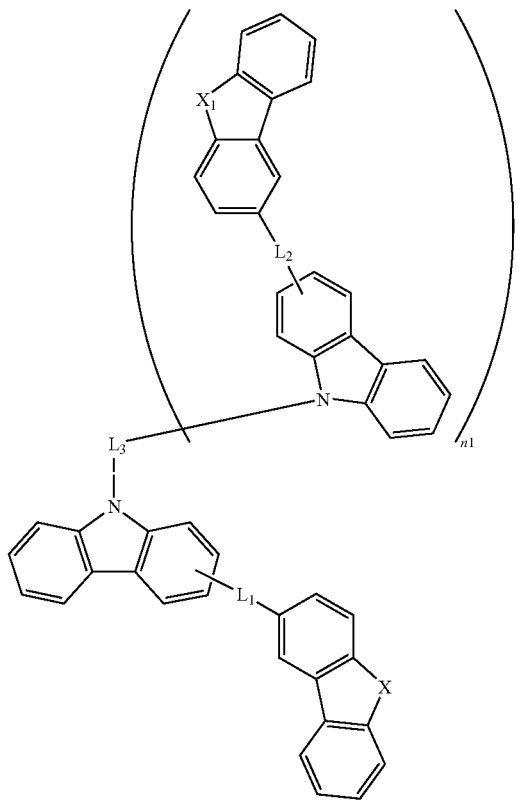

(wherein, $L_1$ and $L_2$ represent a linking group or a simple bond; $L_3$ represents a linking group; X represents O or S; $X_1$ represents O, S, or NRa; n1 represents an integer of 1 to 5; Ra represents a hydrogen atom, an aliphatic group, an aromatic hydrocarbon cyclic group, or a heterocyclic group; and the compound represented by Formula (2) may have a substituent at other position.)

Item 3. An organic electroluminescence element material of the above Item 2, wherein $L_3$ of the above Formula (2) represents a bivalent linking group derived from an aromatic hydrocarbon cyclic group, or a heterocyclic group.

Item 4. An organic electroluminescence element material, wherein the organic electroluminescence element material is represented by Formula (3) below.

Formula (3):

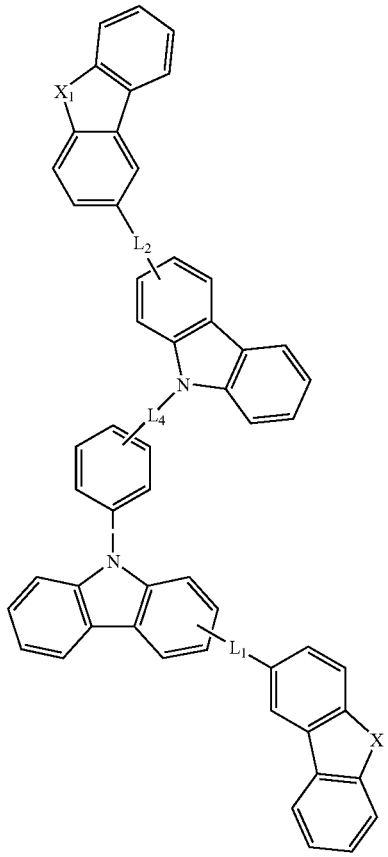

(wherein, $L_1$, $L_2$, and $L_4$ represent a linking group or a simple bond; X represents O or S; $X_1$ represents O, S, or NRa; Ra represents a hydrogen atom, an aliphatic group, an aromatic hydrocarbon cyclic group, or a heterocyclic group; and the compound represented by Formula (3) may have a substituent at other position.)

Item 5. An organic electroluminescence element material, wherein the organic electroluminescence element material is represented by Formula (4) below.

Formula (4):

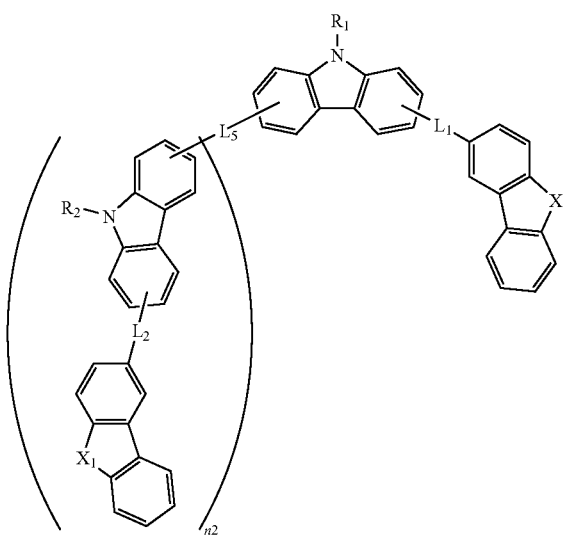

(wherein $R_1$ and $R_2$ represent a hydrogen atom, an aliphatic group, an aromatic hydrocarbon cyclic group, or a heterocyclic group; $L_1$ and $L_2$ represent a linking group or a simple bond; $L_5$ represents a linking group; X represents O or S; $X_1$ represents O, S, or NRa; n2 represents an integer of 1 to 5; Ra represents a hydrogen atom, an aliphatic group, an aromatic hydrocarbon cyclic group, or a heterocyclic group; and the compound represented by Formula (3) may have a substituent at other position.)

Item 6. An organic electroluminescence element material described in the above Item 5, wherein $L_5$ of the above Formula (4) represents a bivalent linking group derived from an aromatic hydrocarbon cyclic group, or a heterocyclic group.

Item 7. An organic electroluminescence element material, wherein the organic electroluminescence element material is represented by Formula (5) below.

Formula (5):

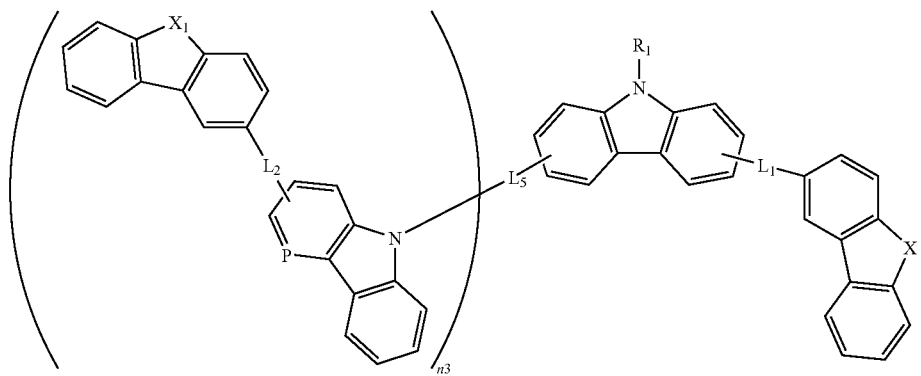

(wherein $R_1$ represents a hydrogen atom, an aliphatic group, an aromatic hydrocarbon cyclic group, or a heterocyclic group; $L_1$ and $L_2$ represent a linking group or a simple bond; $L_6$ represents a linking group; X represents O or S; $X_1$ represents O, S, or NRa; n3 represents an integer of 1 to 5; Ra represents a hydrogen atom, an aliphatic group, an aromatic hydrocarbon cyclic group, or a heterocyclic group; and the compound represented by Formula (3) may have a substituent at other position.)

Item 8. An organic electroluminescence element material described in the above Item 7, wherein $L_6$ of the above Formula (5) represents a bivalent linking group derived from an aromatic hydrocarbon cyclic group, or a heterocyclic group.

Item 9. An organic electroluminescence element material described in any of the above Items 1 to 8, wherein $L_1$, in compounds represented by any of the above Formulae (1) to (5) represents a simple bond.

Item 10. An organic electroluminescence element material described in any of the above Items 1 to 9, wherein X in compounds represented by any of the above Formulae (1) to (5) represents O.

Item 11. An organic electroluminescence element incorporating at least a light-emitting layer which is sandwiched between an anode and a cathode, wherein the organic electroluminescence element incorporates the organic electroluminescence element material described in any of the above Items 1 to 10.

Item 12. An organic electroluminescence element described in the above Item 11, wherein the above light-emitting layer contains a phosphorescent emission dopant.

Item 13. An organic electroluminescence element described in the above Item 12, wherein the 0-0 band of the above phosphorescent emission dopant is not more than 485 nm.

Item 14. An organic electroluminescence element described in any of the above Items 11 to 13, wherein the organic electroluminescence element incorporates an organic electroluminescence element material described in any of the above Items 1 to 10 in the above described light-emitting layer.

Item 15. An organic electroluminescence element described in any of the above Items 11 to 13, wherein the organic electroluminescence element has an electron inhibition layer as a constituting layer, and the aforesaid electron inhibition layer incorporates an organic electroluminescence element material described in any of the above Items 1 to 10.

Item 16. An organic electroluminescence element described in any of the above Items 11 to 13, wherein the organic electroluminescence element has a hole block layer as a constituting layer, and the aforesaid hole inhibition layer incorporates an organic electroluminescence element material described in any of the above Items 1 to 10.

Item 17. An organic electroluminescence element described in any of the above Items 11 to 16, wherein the organic electroluminescence element emits white light.

Item 18. A display devise, wherein the display device is provided with an organic electroluminescence element described in any of the above Items 11 to 17.

Item 19. A lighting apparatus, wherein the lighting apparatus is provided with an organic electroluminescence element described in any of the above Items 11 to 17.

Item 20. A display device, wherein the display device has the lighting apparatus described in the above Item 19, and a liquid crystal element as a display means.

Effects of the Invention

According to the present invention, an organic EL element exhibiting controlled light emission wavelength, high light emission efficiency and long light emission life, an organic EL element material for use thereof, and a lighting apparatus and a display device both of which employ the aforesaid organic EL element were provided.

DESCRIPTION OF NUMERIC DESIGNATIONS

Figure 1:
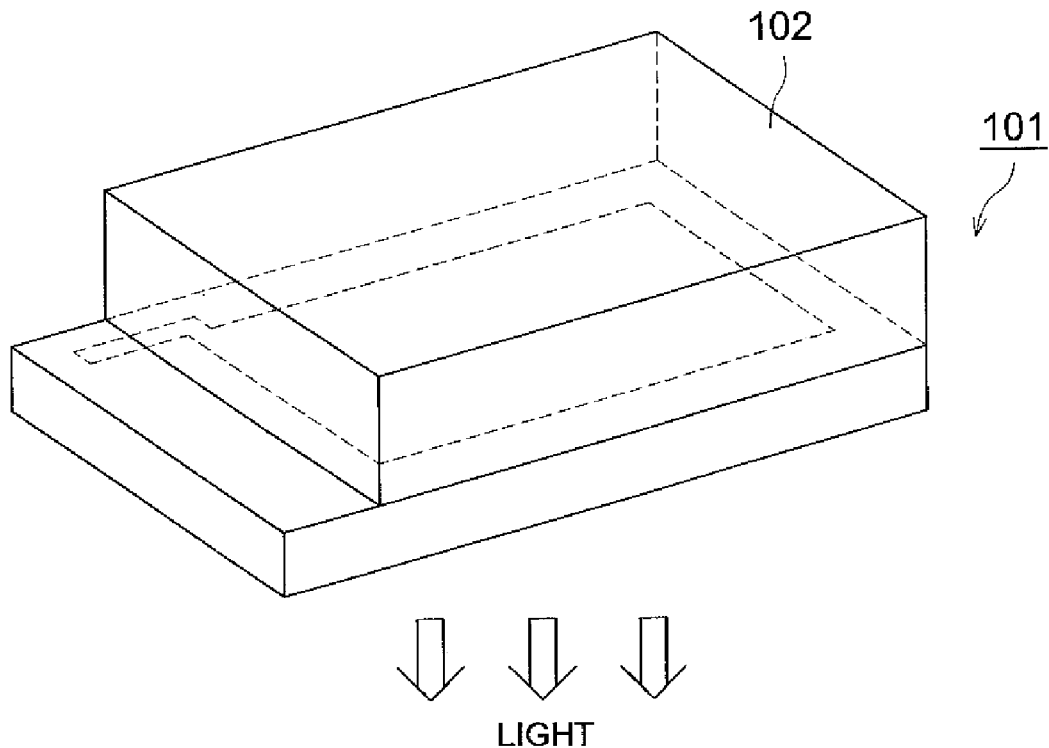
FIG. 1 is a schematic view of the lighting apparatus

101: organic EL element
102: glass cover
107: glass substrate equipped with a transparent electrode
106: organic EL layer
105: cathode
108: nitrogen gas
109: moisture absorbing material

DESCRIPTION OF THE PREFERRED EMBODIMENTS

The organic eleatroluminescence element of the present invention is characterized in that in the organic electroluminescence element incorporating at least a light-emitting layer which is sandwiched between an anode and a cathode, the organic electroluminescence element of the present invention incorporates a compound represented by the above-mentioned Formulae (1) to (5).

<<Compound Represented by Formula (1)>>

In the above Formula (1), $R_1$ represents a hydrogen atom, an aliphatic group, an aromatic hydrocarbon cyclic group, or a heterocyclic group; $L_1$ represents a linking group or a simple bond; X represents O or S; and the compound represented by Formula (1) may have substituents at other positions.

Examples of the aliphatic group represented by $R_1$ in Formula (1) include methyl group, ethyl group, n-propyl group, isopropyl group, t-butyl group, n-octyl group, eicosyl group, 2-chloroethyl group, 2-cyanoethyl group, 2-ethylhexyl group, vinyl group, and allyl group.

Above-described groups may be unsubstituted, or may be further substituted with substituents such that positions in Formula (1) other than the above $R_1$ may have. The above substituents will be described later.

Examples of the aromatic hydrocarbon cyclic group represented by $R_1$ in Formula (1) include phenyl group, o-tolyl group, m-tolyl group, p-tolyl group, naphthyl group, m-chlorophenyl group, 4-dimethylaminophenyl group, o-hexadecanoylaminophenyl group, and naphthyl group.

Above-described groups may be unsubstituted, or may be further substituted with substituents such that positions in Formula (1) other than the above $R_1$ may have. The above substituents will be described later.

Examples of the heterocyclic group represented by $R_1$ in Formula (1) include a non-aromatic heterocyclic group, and an aromatic heterocyclic group. Examples of the non-aromatic heterocyclic group include groups derived from compounds such as an epoxy ring, an aziridine ring, a thiiran ring, an oxetane ring, an azetidine ring, a thietane ring, a tetrahydrofuran ring, a dioxolan ring, a pyrrolizine ring, a pyrazolidine ring, an imidazolidine ring, an oxazolidine ring, a tetrahydrothiophene ring, a sulfolane ring, a thiazolidine ring, an ε-caprolactone ring, a caprolactam ring, a piperidine ring, a hexahydropyridazine ring, a hexahydropyrimidine ring, a piperazine ring, a morpholine ring, a tetrahydropyran ring, an 1,3-dioxane ring, an 1,4-dioxane ring, a trioxane ring, a tetrahydrothiopyran ring, a thiomorpholin ring, a thiomorpholin-1,1-dioxide ring, a pyranose ring, and a diazabicyclo[2,2,2]-octane ring.

Above-described groups may be unsubstituted, or may be further substituted with substituents such that positions in Formula (1) other than the above $R_1$ may have. The above substituents will be described later.

Examples of the aromatic heterocyclic group include a pyridyl group, a pyrimidinyl group, a furyl group, a pyrrolyl group, an imidazolyl group, a benzimidazolyl group, a pyrazolyl group, a pyrazinyl group, a triazyl group (for example, an 1,2,4-triazole-1-yl group, and an 1,2,3-triazole-1-yl group), an oxazolyl group, a benzoxazolyl group, a thiazolyl group, a selenazolyl group, a tetrazolyl group, an isooxazolyl group, an isothiazolyl group, a 3-furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (which indicates one of carbon atoms constituting carboline ring of the above-described carbolinyl group being replaced by a nitrogen atom), a quinoxalinyl group, a pyridazinyl group, a triazinyl group, a quinazolinyl group, a phthalazinyl group.

Above-described groups may be unsubstituted, or may be further substituted with substituents such that positions in Formula (1) other than the above $R_1$ may have. The above substituents will be described later.

A substituent being substituted to such positions in Formula (1) other than the above $R_1$ is as follows. Examples of such a substituent include an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group), a cycloalkyl group (for example, a cyclopentyl group and a cyclohexyl group), an alkenyl group (for example, a vinyl group and an allyl group), an alkynyl group (for example, an ethynyl group and a propargyl group), an aromatic hydrocarbon ring group (also called an aromatic carbon ring group or an aryl group such as a phenyl group, a p-chlorophenyl group, a mesityl group, a tolyl group, a xylyl group, a naphthyl group, an anthryl group, an azulenyl group, an acenaphthenyl group, fluorenyl group, a phenanthryl group, an indenyl group, a pyrenyl group, or a biphenyl group), an aromatic heterocyclic group (for example, a pyridyl group, a pyrimidinyl group, a furyl group, a pyrrolyl group, an imidazolyl group, a benzimidazolyl group, a pyrazolyl group, a piradinyl group, a triazolyl group (for example, a 1,2,4-triazole-1-yl group and a 1,2,3-triazole- 1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolynyl group, a diazacarbazoyl group (which shows that one of the carbon atoms which constitute a carboline ring of the above carbolinyl group is replaced with a nitrogen atom), a quinoxythalinyl group, a pyridazinyl group, a triazinyl group, a quinazolinyl group, a phthalazinyl group), a heterocyclic group (for example, a pyrrolidinyl group, an imidazolidyl group, a morpholyl group, and an oxazolidyl group), an alkoxy group (for example, a methoxy group, an ethoxy group, a propyloxy group, a pentyloxy group, a hexyloxy group, an octyloxy group, and a dodedyloxy group), a cycloalkoxy group (for example, a cyclopentyloxy group and a cyclohexyloxy group), an aryloxy group (for example, a phenoxy group and a naphthyloxy group), an alkylthio group (for example, a methylthio group, an ethylthio group, a propylthio group, a pentylthio group, a hexylthlio group, an octylthio group, and a dodecylthio group), a cycloalkylthio group (for example, a cyclopentylthio group and a cyclohexylthio group), an arylthio group (for example, a phenylthio group and a naphthylthio group), an alkoxycarbonyl group (for example, a methyloxycarbonyl group, an ethyloxycarbonyl group, a butyloxycarbonyl group, an octyloxycarbonyl group, and a dodecyloxycarbonyl group), an aryloxycarbonyl group (for example, a phenyloxycarbonyl group and a naphthyloxycarbonyl group), a sultamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group), an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, a pyridylcarbonyl group), an acyloxy group (for example, an acetyloxy group, an ethylcarbonyloxy group, a butylcarbonyloxy group, an octylcarbonyloxy group, a dodecylcarbonyloxy group, and a phenylcarbonyloxy group), an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminodarbonyl group, and a 2-pyridylaminocarbonyl group), an ureido group (for example, a methylureido group, an ethylureido group, a pentylureido group, a cyclohexylureido group, an octylureido group, a dodecylureido group, a phenylureido group, a naphthylureido group, and a 2-pyridylaminoureido group), a sulfinyl group (for example, a methylsulfinyl group, an ethylsulfinyl group, a butylsulfinyl group, a cyclohexylsulfinyl group, a 2-ethylhexylsulfinyl group, a docecylsulfinyl group, a phenylsulfinyl group, a naphthylsulfinyl group, and a 2-pyridylsulfinyl group), an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group), an arylsulfonyl group or a heteroarylsulfonyl group (for example, a phenylsulfonyl group, a naphthylsulfonyl group, and a 2-pyridylsulfonyl group), an amino group (for example, an amino group, an ethylamino group, a dimethylamino group, a butylamino group, a cyclopentylamino group, a 2-ethylhexylamino group, a dodecylamino group, an anilino group, a cyclopentylamino group, a 2-ethylhexylamino group, a dodecylamino group, an anilino group, a naphthylamino group, and a 2-pyridylamino group), a halogen atom (for example, a fluorine atom, a chlorine atom, and a bromine atom), a fluorinated hydrocarbon group (for example, a fluoromethyl group, a trifluoromethyl group, a pentafluoroethyl group, and a pentafluorophenyl group), a cyano group, a nitro group, a, hydroxyl group, a mercapto group, and a silyl group (for example, a trimethylsilyl group, a triisopropylsilyl group, a triphenylsilyl group, and a phenyldiethylsilyl group). These groups may further have substituents.

The divalent linking groups represented by each of $L^1$ in Formulas (1) may include an alkylene group (for example, an ethylene group, a trimethylene group, a tetramethylene group, a propylene group, an ethylethylene group, a pentamethylene group, and a hexamethylene group); an alkenylene group (for example, a vinylene group, a propenylene group, a butenylene group, a pentenylene group, a 1-methylvinylene group, a 1-methylpropenylene group, a 2 methylpropenylene group, a 1-methylpentenylene group, a 3-methylpentenylene group, a 1-ethylvinylene group, a 1-ethylpropenylene group, a 1-ethylbutenylene group, and a 3 ethylbutenylene group); an alkynylene group (for example, an ethynylene group, a propynylene group, a 1-butynylene group, a 1-pentynylene group, a 1-hexynylene group, a 2-butynylene group, a 2-pentynylene group, a 1-methylethynylene group, a 3-methyl-1-propynylene group, and a 3-methyl-1-butynylene group); an arylene group (for example, an o-phenylene group, an m-phenylene group, a p-phenylene group, a naphthalenediyl group, an anthracenediyl group, a naphthacenediyl group, a pyrenediyl group, a naphthylnaphthalenediyl group, a biphenyldiyl group (for example, a [1,1'-biphenyl]-4,4'-diyl group, a 3,3'-biphenyldiyl group, and a 3,6-biphenyldiyl group); a terphenyldiyl group, a quaterphenyldiyl group, a kinkphenyldiyl group, a sequsiphenyldiyl group, a septiphenyldiyl group, an octiphenyldiyl group, a noviphenyldiyl group, and a deciphenyldiyl group); a heteroarylene group (for example, a carbazole ring, a carboline ring, a diazacarbazole ring (which is also called a monoazacarboline ring, and refers to a ring structure in which one of carbon atoms which constitutes a carboline ring is replaced with a nitrogen atom), a divalent group derived from the group consisting of a triazole ring, a pyrrole ring, a pyrazine ring, a quinoxaline ring, a thiophene ring, an oxadiazole ring, a dibenzofuran ring, a benzothiophene ring, and an indole); a divalent heterocyclyl group (for example, a divalent group derived from a pyrrolidine ring, an imidazoline ring, a morpholine ring, and an oxazolidine ring); and a chalcogen atom such as oxygen or sulfur.

Further, applicable may be groups such as an alkylimino group, a dialkylsilanediyl group, or a diarylgermanediyl group which are linked via a heteroatom.

The simple bond is the one which directly bonds linking substituents each other.

<<<Compound Represented by Formula (2)>>>

In the above Formula (2), $L_1$ and $L_2$ represent a linking group or a simple bond; $L_3$ represents a linking group; X represents O or S; $X_1$ represents O, S, or NRa; n1 represents an integer of 1 to 5; Ra represents a hydrogen atom, an aliphatic group, an aromatic hydrocarbon cyclic group, or a heterocyclic group; and the compound represented by Formula (2) may have substituents at other positions.

The linking group or the simple bond represented by $L_1$ or $L_2$, and the linking group represented by $L_3$ are the same as those represented by $L_1$ of Formula (1). The aliphatic group, the aromatic hydrocarbon cyclic group, or the heterocyclic group represented by Ra is also the same as those represented by $R_1$ of Formula (1). Regarding the substituents at other positions, they are also the same as those of Formula (1).

In Formula (2), the linking group represented by $L_3$ is preferably a bivalent linking group derived from an aromatic hydrocarbon ring, or a heterocyclic ring. Specific examples of the aromatic hydrocarbon ring include benzene, toluene, naphthalene, chlorobenzene, dimethylaminobenzene; and specific examples of heterocyclic ring include pyridine, thiazole, oxazole, imidazole, furan, thiophene, pyrimidine, pyridazine, selenazole, pyrazole, and tetrazole.

<<Compound Represented by Formula (3)>>

In the above Formula (3), $L_1$, $L_2$ and $L_4$ represent a linking group or a simple bond; X represents O or S; $X_1$ represents O, S, or NRa; Ra represents a hydrogen atom, an aliphatic group, an aromatic hydrocarbon cyclic group, or a heterocyclic group; and the compound represented by Formula (3) may have substituents at other positions.

The linking group or the simple bond represented by $L_1$ $L_2$, or $L_4$ is the same as that represented by $L_1$ of Formula (1) The aliphatic group, the aromatic hydrocarbon cyclic group, or the heterocyclic group represented by Ra is also the same as those represented by $R_1$ of Formula (1). Regarding the substituents at other positions, they are also the same as those of Formula (1).

<<Formula (4)>>

In Formula (4), $R_1$ and $R_2$, represent a hydrogen atom, an aliphatic group, an aromatic hydrocarbon cyclic group, or a heterocyclic group; $L_1$ and $L_2$ represent a linking group or a simple bond; $L_5$ represents a linking group; X represents O or S; $X_1$ represents O, S, or NRa; n2 represents an integer of 1 to 5; Ra represents a hydrogen atom, an aliphatic group, an aromatic hydrocarbon cyclic group, or a heterocyclic group; and the compound represented by Formula (4) may have substituents at other positions.

In Formula (4), the aliphatic group, the aromatic hydrocarbon cyclic group, or the heterocyclic group represented by $R_1$, $R_2$, or Ra is the same as that represented by $R_1$ of Formula (1). The linking group or the simple bond represented by $L_1$ or $L_2$, and the linking group represented by $L_5$ are the same as that described as $L_1$ of Formula (1). Regarding the substituents at other positions, they are also the same as those of Formula (1).

In Formula (4), the linking groups represented by $L_5$ are preferably bivalent linking groups derived from an aromatic hydrocarbon ring, or a heterocyclic ring. Specific examples of the aforesaid aromatic hydrocarbon ring and heterocyclic ring are listed as those of $L_3$ of Formula (2).

<<Formula (5)>>

In the above-described Formula (5), $R_1$ represents a hydrogen atom, an aliphatic group, an aromatic hydrocarbon cyclic group, or a heterocyclic group; $L_1$ and $L_2$ represent a linking group or a simple bond; $L_6$ represents a linking group; X represents O or S; $X_1$ represents O, S, or NRa; n3 represents an integer of 1 to 5; Ra represents a hydrogen atom, an aliphatic group, an aromatic hydrocarbon cyclic group, or a heterocyclic group; and the compound represented by Formula (5) may have substituents at other positions.

In Formula (5), the aliphatic group, the aromatic hydrocarbon cyclic group, or the heterocyclic group represented by $R_1$ or Ra is the same as that represented by $R_1$ of Formula (1). The linking group or the simple bond represented by $L_1$ or $L_2$, and the linking group represented by L6 are the same as that described in $L_1$ of Formula (1). Regarding the substituents at other positions, they are also the same as those of Formula (1).

In Formula (5), the linking groups represented by $L_6$ are preferably bivalent linking groups derived from an aromatic hydrocarbon ring, or a heterocyclic ring. Specific examples of the aforesaid aromatic hydrocarbon ring and heterocyclic ring are listed as those of $L_3$ of Formula (2).

In the above-described Formula (1) to (5), $L_1$ is preferably a simple bond, and X is preferably O.

Specific examples of the compounds represented by Formula (1) to (5) are listed below, but the present invention is not limited to them.

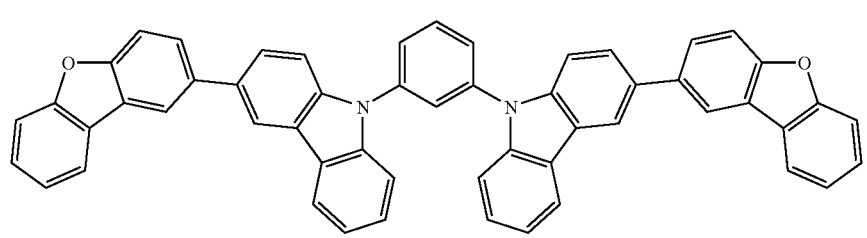

(1)

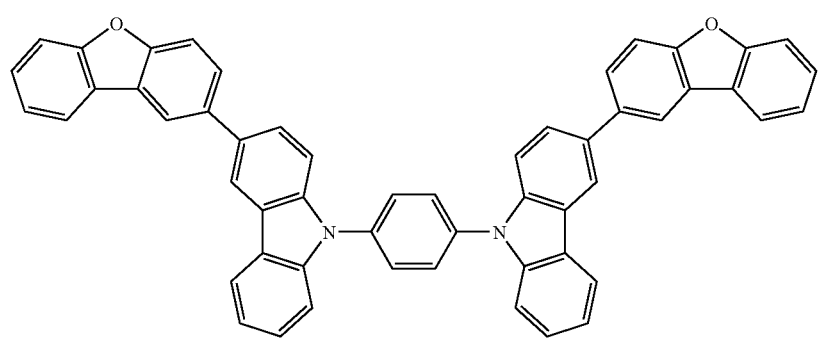

(2)

-continued
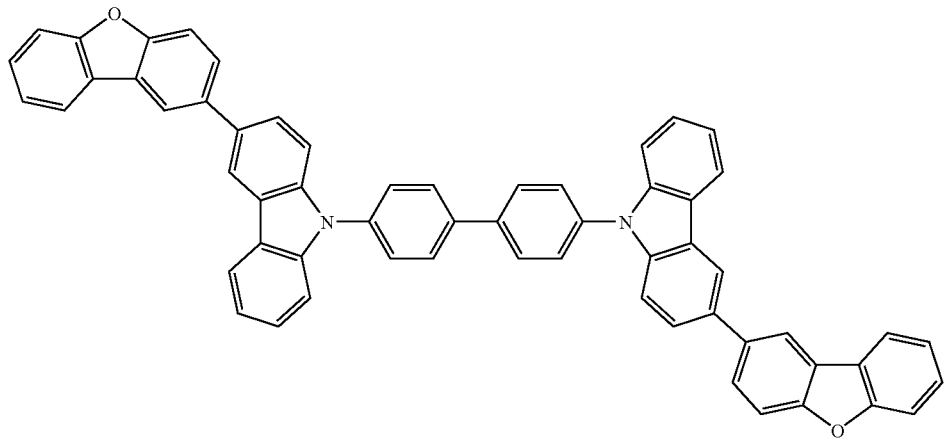
(3)
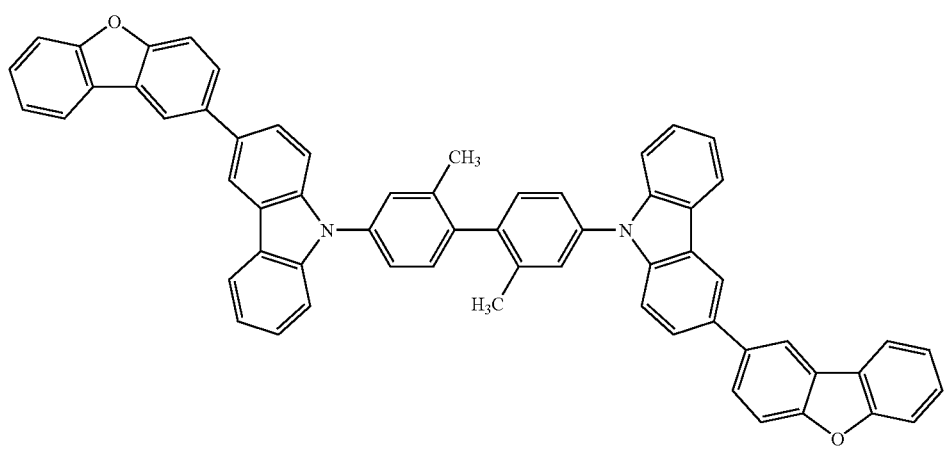
(4)
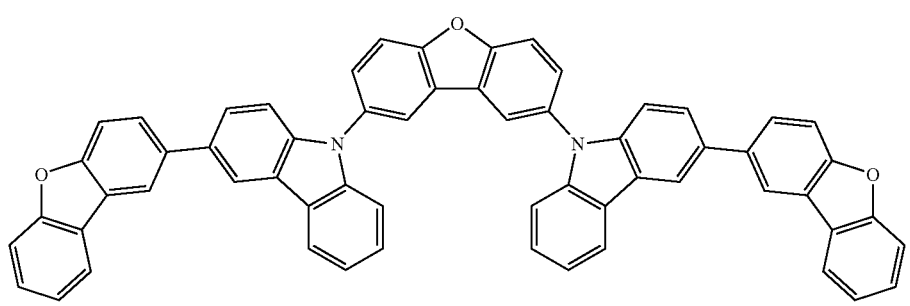
(5)
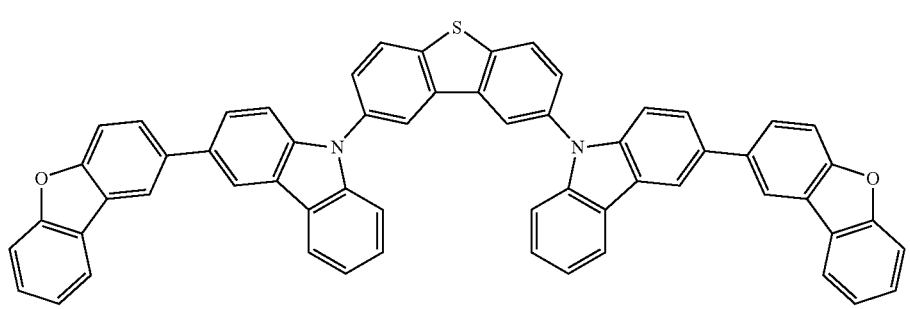
(6)

(7)
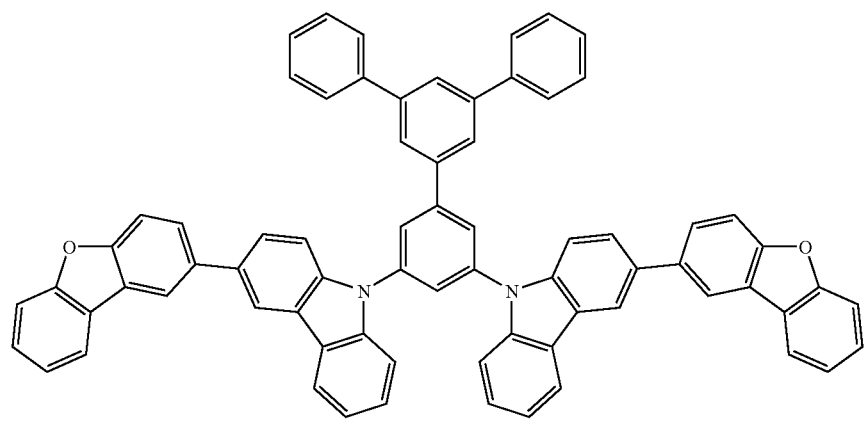
(8)
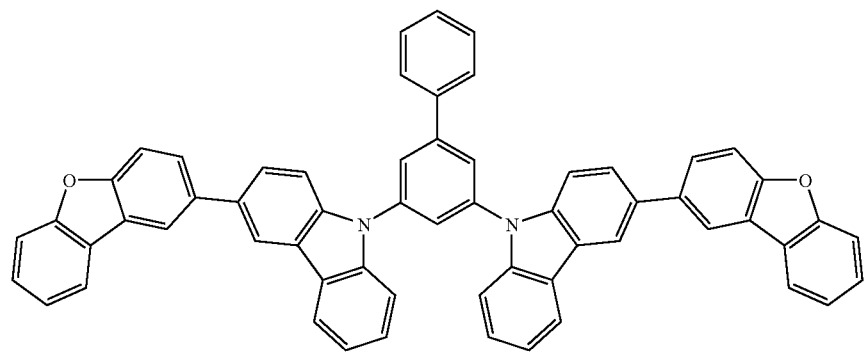
(9)
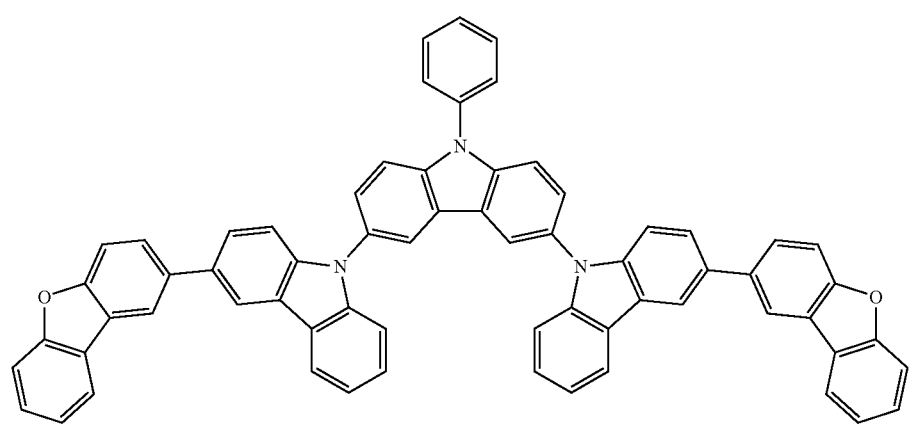

-continued
(10)
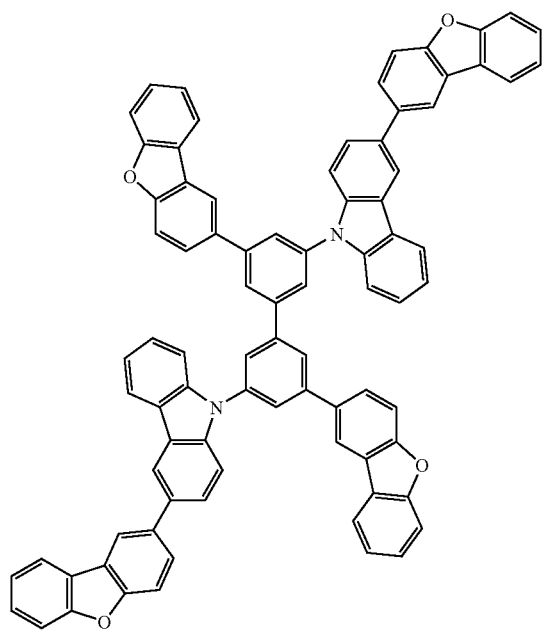
(11)
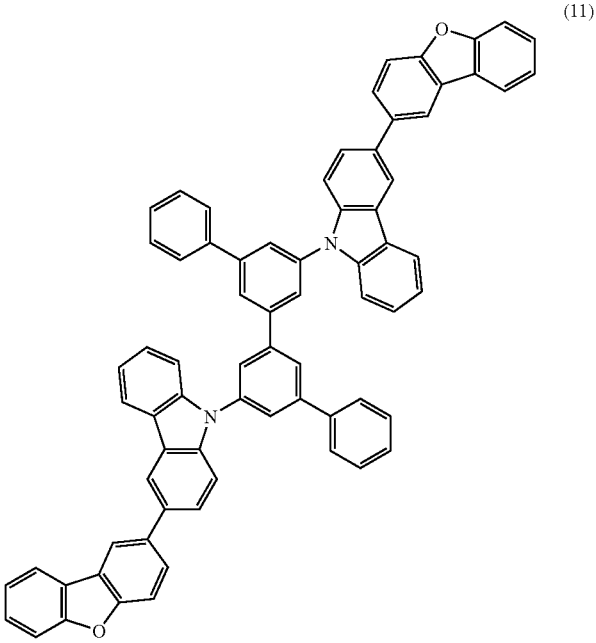
(12)
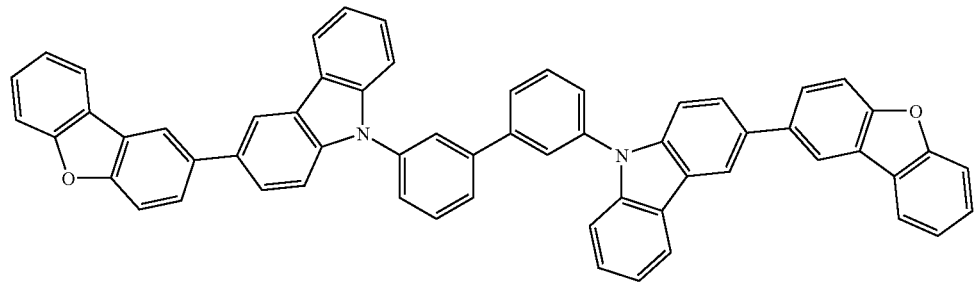
(13)
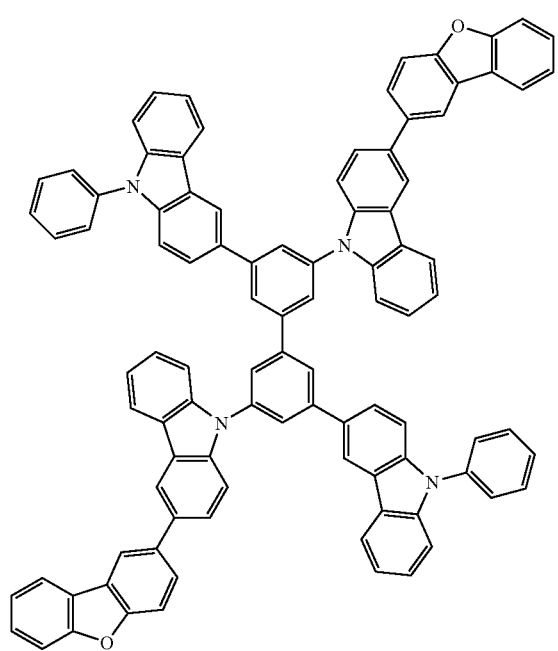
(14)
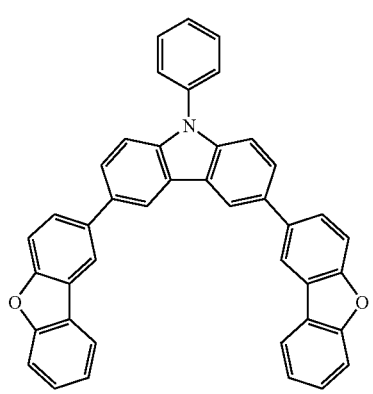

(15)
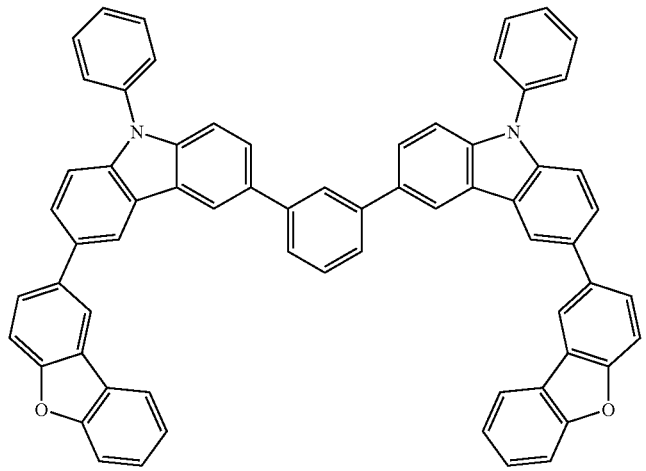
(16)
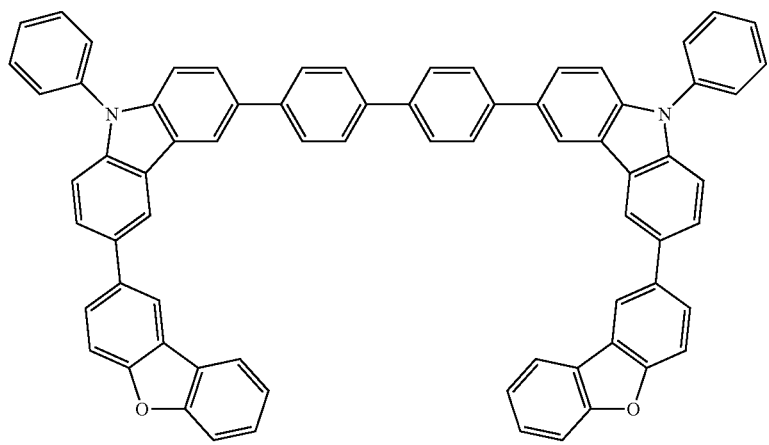
(17) (18)
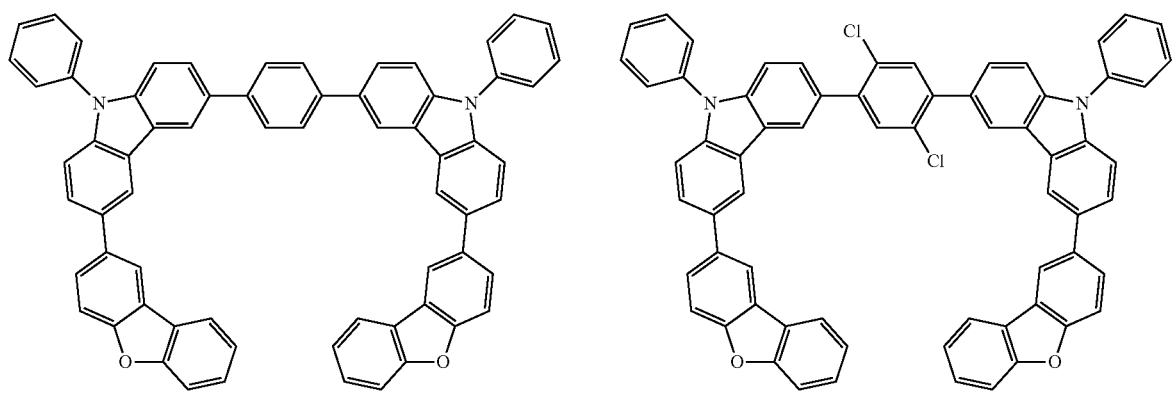
(19)
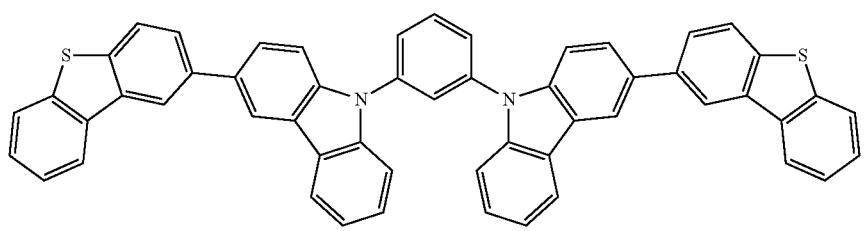

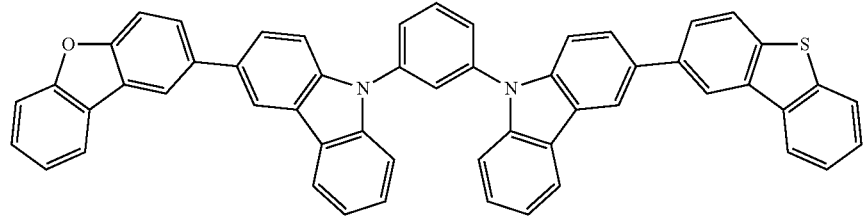
(20)
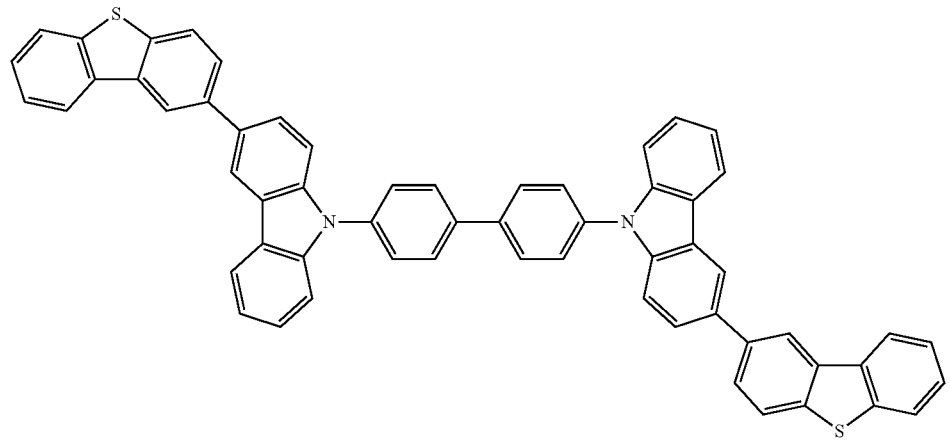
(21)
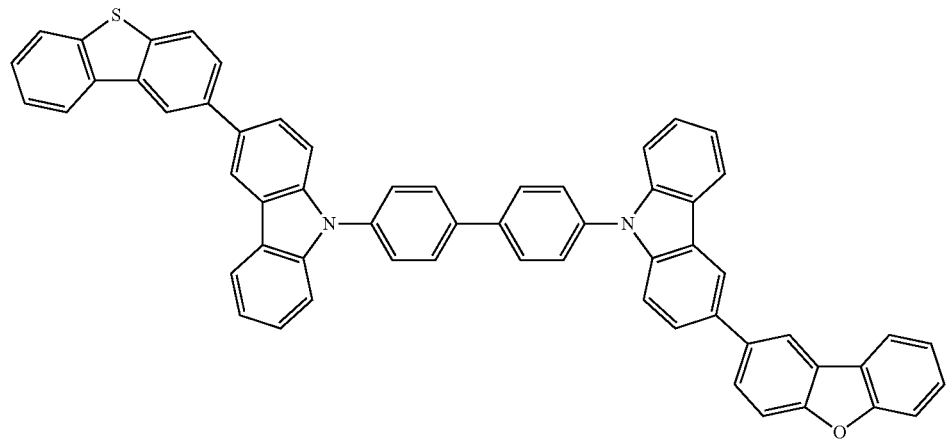
(22)
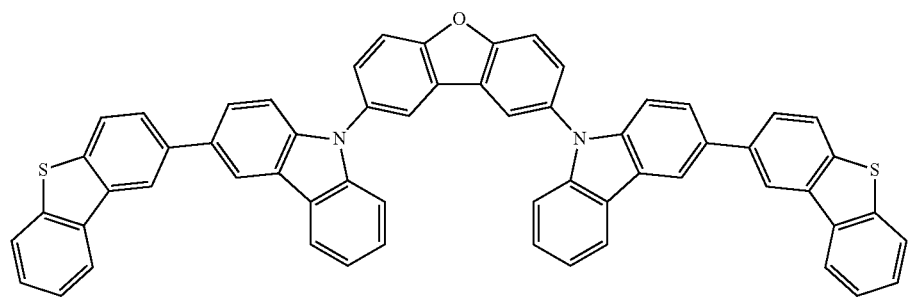
(23)

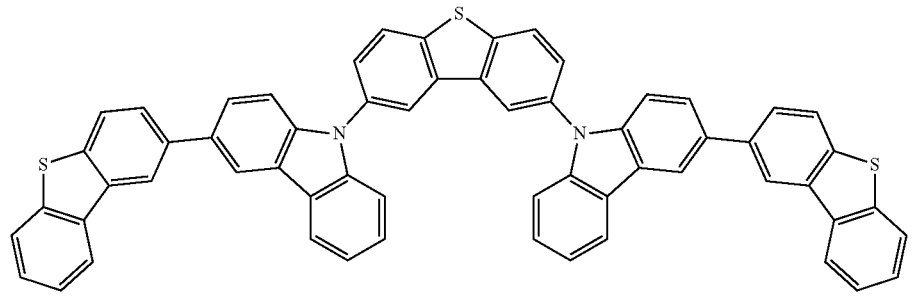
(24)
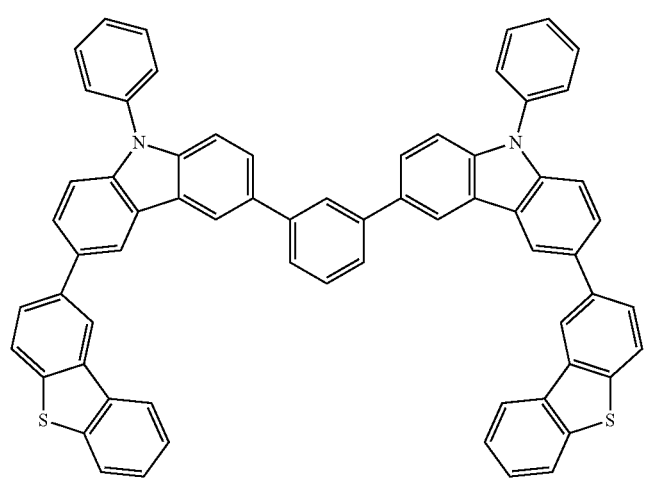
(25)
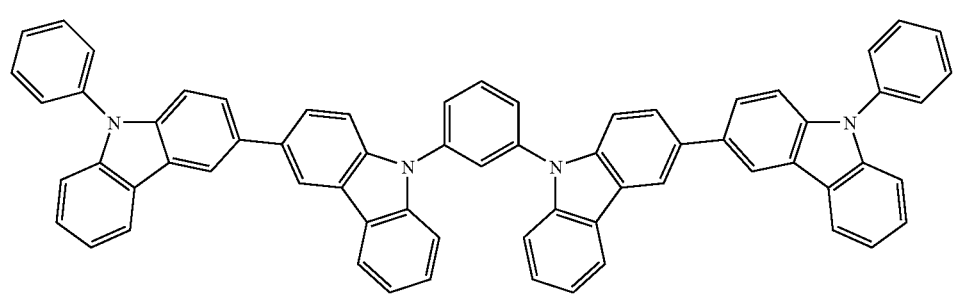
(26)

-continued
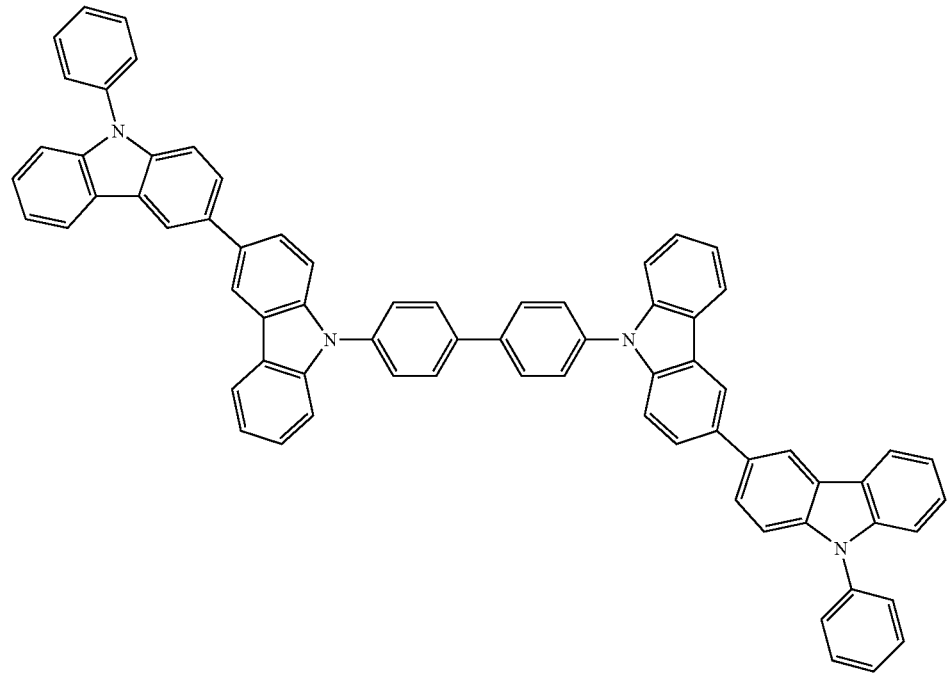
(27)
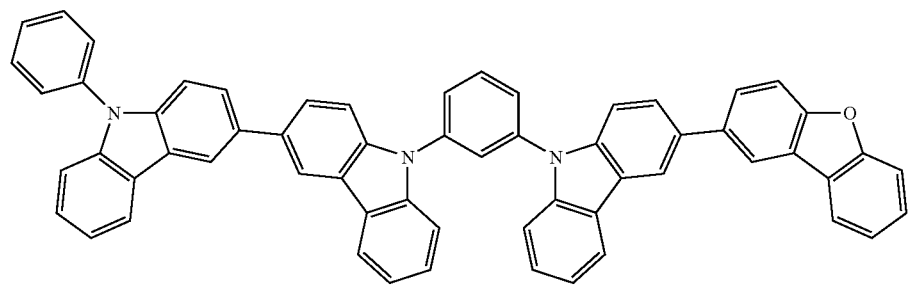
(28)
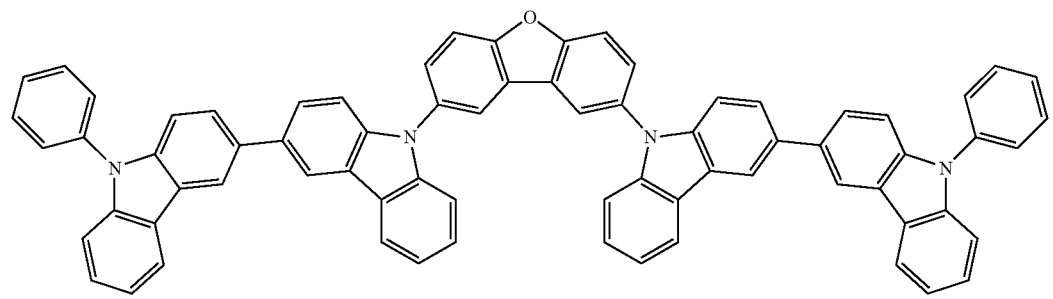
(29)

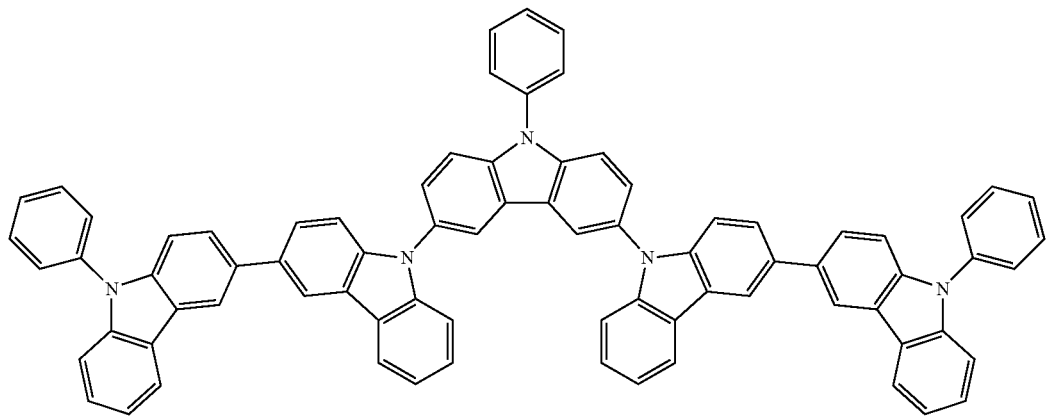
(30)
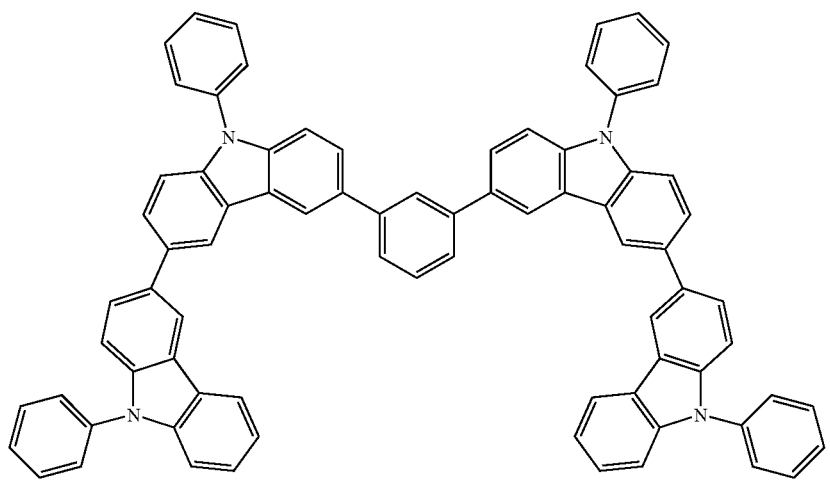
(31)
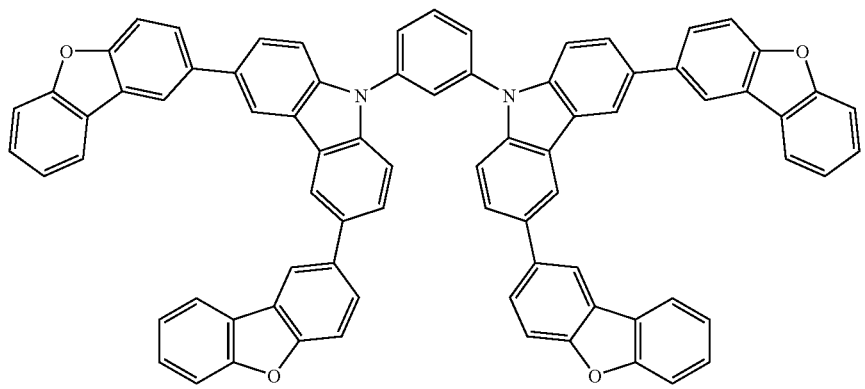
(32)

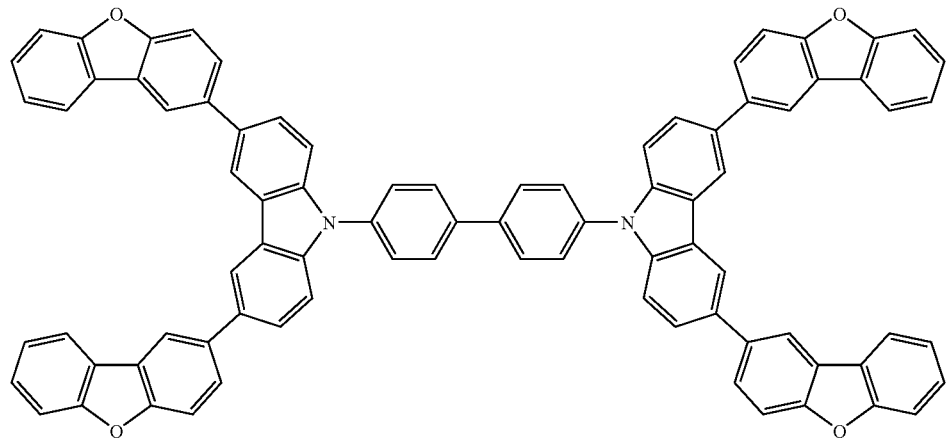
(33)
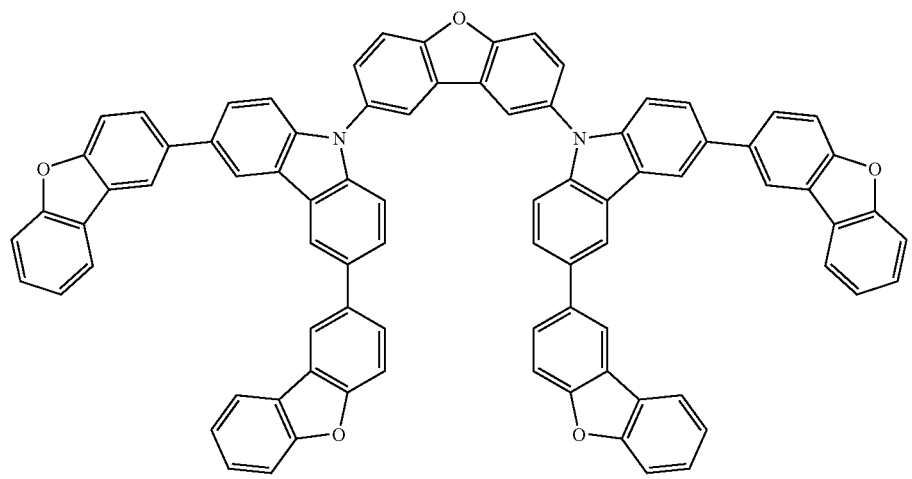
(34)
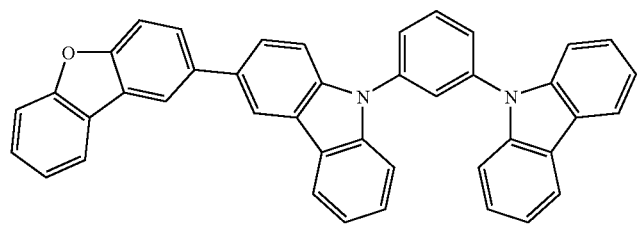
(35)
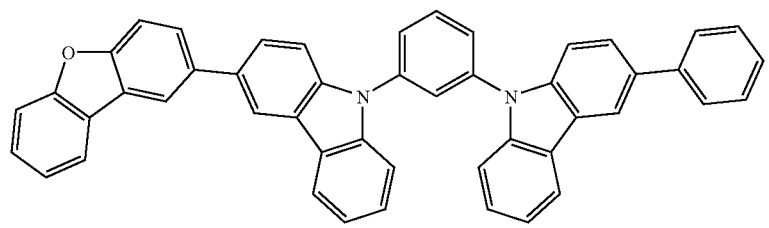
(36)

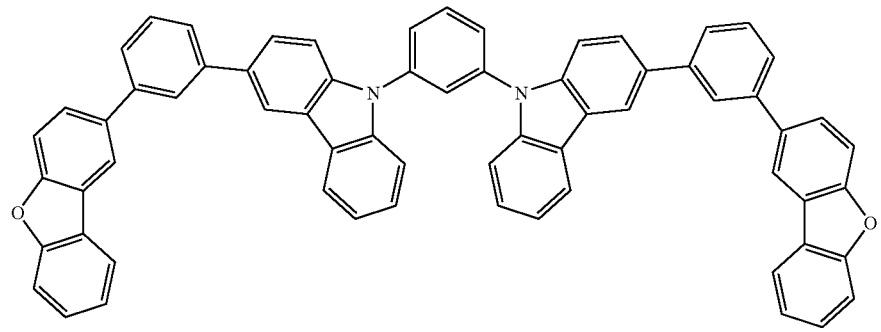
(37)
Representative syntheses of compounds represented by Formulae (1) to (5) are described below.
Synthesis of Exemplified Compound (1)
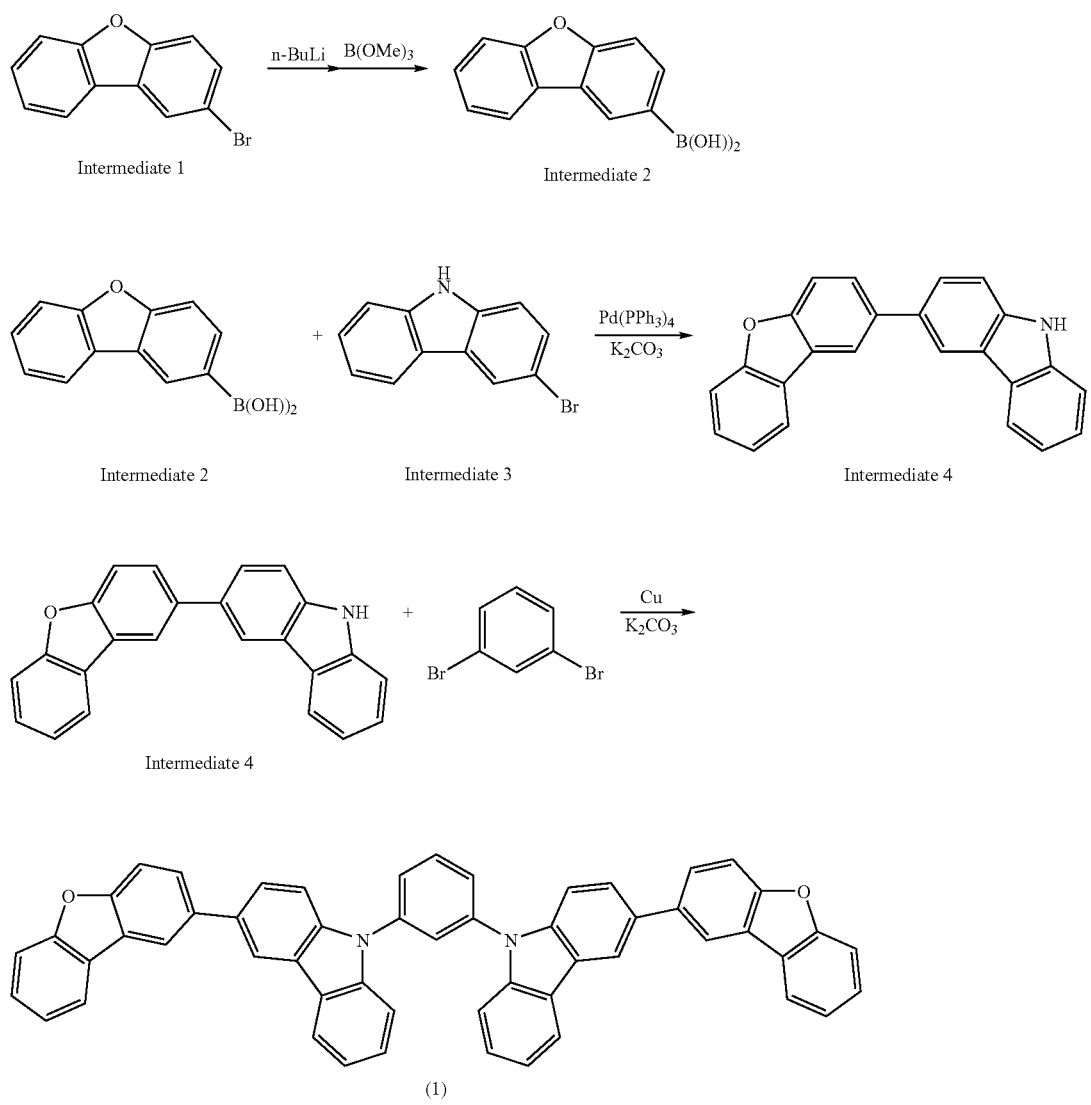
(1)

Synthesis of Intermediate 2

Into a 500 ml three-necked flask, 24.7 g of Intermediate 1 was put, and then, under a nitrogen gas flow, 300 ml of THF (dehydrated) was charged into the flask using a syringe. The solution was cooled in a bath containing acetone and dry ice, and 76.2 ml of n-BuLi (1.6 mol/l) was added dropwise into the flask at −60° C. or lower. After being stirred at −60° C. or lower for one hour, a mixed solution of 24.0 g of trimethoxyborane and 30 ml of THF (dehydrated) was added dropwise into the flask. After that, the temperature of the resulting solution was raised to a room temperature, and then the solution was stirred for two hours. Further, 150 ml of 10% HCl solution was added, and then the resulting solution was introduced into a separatory funnel, washed with water three times, and then dewatered using $MgSO_4$. After the $MgSO_4$ was filtered out, the resulting solution was concentrated to a solid, which was then washed with n-hexane to provide 10.5 g of Intermediate 2.

Synthesis of Intermediate 4

Into a 500 ml three-necked flask, 9.5 g of Intermediate 2 and 10 g of Intermediate 3 were put, and then, under a nitrogen gas flow, 250 ml of THF was charged into the flask. Further, a solution of 8.5 g of $K_2CO_3$ dissolved in 75 ml of water was added to the flask, followed by addition of 4.5 g of $Pd(PPh_3)_4$, and then the mixture was subjected to a reaction while refluxing for 10 hours. After the reaction, the resulting solution was introduced into a separatory funnel, washed with water three times, and then dewatered using $MgSO_4$. After the $MgSO_4$ was filtered out, the resulting solution was concentrated to a solid. The resulting solid was subjected to silica gel chromatography employing a hexane/ethylacetate=8/1 mixture as a developing solvent to provide 5.6 g of Intermediate 4.

Synthesis of Exemplified Compound (1)

Into a 300 ml three-necked flask, 3.6 g of Intermediate 4, 1.2 g of m-dibromobenzene, 150 ml of dimethylacetamide, 0.85 g of copper powder, and 2.1 g of $K_2CO_3$ were added, and the mixture solution was subjected to a reaction at the solution temperature of 150° C. for 8 hours. To the resulting solution, water and ethylacetate were added. The mixture solution was introduced into a separatory funnel, the organic layer was washed with water three times, and then dewatered using $MgSO_4$. After the $MgSO_4$ was filtered out, the resulting solution was concentrated to a solid. The resulting solid was subjected to silica gel chromatography employing a hexane/ethylacetate=10/1 mixture as a developing solvent to provide 1.1 g of Exemplified Compound (1). The structure of Exemplified Compound (1) was determined via $^1$H-NMR as described below.

$^1$H-NMR (400 MHz, $CDCl_3$): 8.44(2H, d), 8.26(4H, m), 8.05(2H, d), 7.92(2H, m), 7.79(6H, m), 7.68(4H, d), 7.51(4H, d), 7.50(4H, m), 7.38(4H, m)

Other compounds can be synthesized in a similar manner.

These compounds are preferably employed as a host compound in an undermentioned light-emitting layer, and also employed in an electron inhibition layer and a hole inhibition layer.

Typical constitutions of an organic EL element of the present invention will be described. Specific examples of a preferable layer constitution of an organic EL element of this invention are shown below; however, the present invention is not limited thereto.

(i) anode/emission layer/electron transport layer/cathode,
(ii) anode/positive hole transport layer/emission layer/electron transport layer/cathode,
(iii) anode/positive hole transport layer/emission layer/positive hole inhibition layer/electron transport layer/cathode,
(iv) anode/positive hole transport layer/emission layer/positive hole inhibition layer/electron transport layer/cathode buffer layer/cathode,
(v) anode/anode buffer layer/positive hole transport layer/emission layer/positive hole inhibition layer/electron transport layer/cathode buffer layer/cathode, The positive hole inhibition layer is also called a hole block layer, and substantially constituted with an electron transporting material. Therefore, the electron transport layer and the positive hole inhibition layer may be constituted as one layer.

It is preferable that the organic EL element of the present invention incorporates monochromatic light emitting layers, namely a blue light emitting layer which emits light at a maximum wavelength in the range of preferably 430-480 nm, a green light-emitting layer which emits light having a maximum wavelength in the range of preferably 510-550 nm, and a red light emitting layer which emits light having a maximum wavelength in the range of preferably 600-640 nm, and display devices are prepared employing the above. Further, these three layers may be laminated to prepare a white light emitting layer. Further, a non-light emitting interlayer may be incorporated between the light emitting layers. It is preferable that the organic EL element of the present invention is composed of a white light emitting layer and that illuminating devices are composed of the same.

Each layer which constitutes the organic EL element of the present invention will now be described.

<Anode>

As an anode according to an organic EL element of this invention, those comprising metal, alloy, a conductive compound, which is provided with a large work function (not less than 4 eV), and a mixture thereof as an electrode substance are preferably utilized. Specific examples of such an electrode substance include a conductive transparent material such as metal like Au, CuI, indium tin oxide (ITO), $SnO_2$ and ZnO. Further, a material such as IDIXO ($In_2O_3$—ZnO), which can prepare an amorphous and transparent electrode, may be also utilized.

As for an anode, these electrode substances may be made into a thin layer by a method such as evaporation or spattering and a pattern of a desired form may be formed by means of photolithography, or in the case of requirement of pattern precision is not so severe (not less than 100 μm), a pattern may be formed through a mask of a desired form at the time of evaporation or spattering of the above-described substance.

In the case of using coatable substances such as organic conductive compound, a wet film making process such as a printing method and a coating method may be utilized. When emission is taken out of this anode, the transmittance is preferably set to not less than 10% and the sheet resistance as an anode is preferably not more than a few hundreds Ω/□. Further, although the layer thickness depends on a material, it is generally selected in a range of 10-1,000 nm and preferably of 10-200 nm.

<Cathode>

On the other hand, as a cathode according to this invention, metal, alloy, a conductive compound and a mixture thereof, which have a small work function (not more than 4 eV), are utilized as an electrode substance.

Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal.

Among them, with respect to an electron injection property and durability against such as oxidation, preferable are a mixture of electron injecting metal with the second metal which is stable metal having a work function larger than electron injecting metal, such as a magnesium/silver mixture, a magnesium/aluminum mixture, a magnesium/indium mixture, an aluminum/aluminum oxide ($Al_2O_3$) mixture and a lithium/aluminum mixture, and aluminum.

As for a cathode, these electrode substances may be made into a thin layer by a method such as evaporation or spattering. Further, the sheet resistance as a cathode is preferably not more than a few hundreds $\Omega/\square$ and the layer thickness is generally selected in a range of 10 nm-5 μm and preferably of 50-200 nm. Herein, to transmit emission, either one of an anode or a cathode of an organic EL element is preferably transparent or translucent to improve the mission luminance.

Further, after preparing the above 1-20 nm thick metal film on the cathode, electrically conductive transparent materials listed in the description of the anode are applied thereon, whereby it is possible to prepare a transparent or translucent cathode. By employing this, it is possible to prepare an element in which both the anode and cathode exhibit transmitting properties.

An injection layer, an inhibition layer, and an electron transporting layer, which are employed as a constituting layer of the organic EL element of the present invention, will now be described.

<Injection Layer>: Electron Injection Layer, Positive Hole Injection Layer

An injection layer is appropriately provided and includes an electron injection layer and a positive hole injection layer, which may be arranged between an anode and an emission layer or a positive transfer layer, and between a cathode and an emission layer or an electron transfer layer, as described above.

An injection layer is a layer which is arranged between an electrode and an organic layer to decrease an operating voltage and to improve an emission luminance, which is detailed in volume 2, chapter 2 (pp. 123-166) of "Organic EL Elements and Industrialization Front thereof (Nov. 30, 1998, published by N. T. S Corp.)", and includes a positive hole injection layer (an anode buffer layer) and an electron injection layer (a cathode buffer layer).

An anode buffer layer (a positive hole injection layer) is also detailed in such as JP-A 9-45479, 9-260062 and 8-288069, and specific examples include such as a phthalocyanine buffer layer comprising such as copper phthalocyanine, an oxide buffer layer comprising such as vanadium oxide, an amorphous carbon buffer layer, and a polymer buffer layer employing conductive polymer such as polythiophene.

A cathode buffer layer (an electron injection layer) is also detailed in such as JP-A 6-325871, 9-17574 and 10-74586, and specific examples include a metal buffer layer comprising such as strontium and aluminum, an alkali metal compound buffer layer comprising such as lithium fluoride, an alkali earth metal compound buffer layer comprising such as magnesium fluoride, and an oxide buffer layer comprising such as aluminum oxide. The above-described buffer layer (injection layer) is preferably a very thin layer, and the layer thickness is preferably in a range of 0.1 nm-5 μm although it depends on a raw material.

<Positive Hole Inhibition Layer>

As a positive hole inhibition layer, for example, a positive inhibition layer described in such as JP-A Nos. 11-204258 and 11-204359 and p. 237 of "Organic EL Elements and Industrialization Front Thereof (Nov. 30 (1998), published by N. T. S Corp.)" is applicable to a positive hole inhibition (hole block) layer according to this invention.

A positive hole inhibition layer, in a broad meaning, is provided with a function of electron transport layer, being comprised of a material having a function of transporting an electron but a very small ability of transporting a positive hole, and can improve the recombination probability of an electron and a positive hole by inhibiting a positive hole while transporting an electron. Further, a constitution of an electron transport layer described later can be appropriately utilized as a positive hole inhibition layer according to this invention.

It is preferable that the positive hole inhibition layer of the organic EL element of the present invention is arranged adjacent to the light emitting layer.

It is preferable that the positive hole inhibition layer (hole block layer) incorporates the compounds represented by above Formula (1)-(5).

Further, in the present invention, in the presence of a plurality of light emitting layers which emit a plurality of different colors of light, it is preferable that the light emitting layer which emits the maximum amount of light of the shortest wavelength of all the light emitting layers, is nearest the anode. In such a case, it is preferable that a positive hole inhibition layer is additionally arranged between the above shortest wavelength light emitting layer and the light emitting layer which is nearest the anode, except for the above layer. Further, it is preferable that an ionization potential of at least 50% by weight of the compounds, incorporated in the positive hole inhibition layer arranged in the above position, is 0.3 eV higher than that of the host compounds of the above shortest wavelength light emitting layer.

Ionization potential is defined as energy required to transfer an electron in the HOMO (highest occupied molecular orbital) to the vacuum level, and is determined by the methods described below:

(1) it is possible to determine ionization potential in such a manner that the value, which is calculated by performing structural optimization by employing Gaussian 98 (Gaussian 98, Revision A. 11.4, M J. Frisch, et al., Gaussian, Inc., Pittsburgh Pa., 2002) and B3LYP/6-31G* as a key word, and the calculated value (being the value in terms of eV unit) is rounded off at the second decimal place. Background in which the above calculated value is effective is that the calculated values obtained by the above method and experimental values exhibit high correlation.

(2) it is also possible to obtain ionization potential via a direct measurement method employing a photoelectron spectroscopy. For example, it is possible to appropriately employ a low energy electron spectrometer "Model AC-1", produced by Riken Keiki Co., Ltd., or a method known as ultraviolet photoelectron spectroscopy.

On the other hand, an electron inhibition layer is, in a broad meaning, provided with a function of a positive hole transport layer, being comprised of a material having a function of transporting a positive hole but a very small ability of transporting an electron, and can improve the recombination probability of an electron and a positive hole by inhibiting an electron while transporting a positive hole.

The compounds represented by Formula (1) to (5) in the present invention are preferably employed in an electron inhibition layer.

Further, a constitution of a positive hole transport layer described later can be appropriately utilized as an electron inhibition layer.

The layer thickness of a positive hole inhibition layer and an electron transport layer of the present invention is preferably in a range of 3-100 nm, more preferably in a range of 5-30 nm.

<<Light Emitting Layer>>

The light emitting layer according to the present invention results in light emission via recombination of electrons and positive holes injected from the electrode or the electron transporting layer, and the positive hole transporting layer, and the light emitting portion may be in the interior of the light emitting layer or at the interface between the light emitting layer and the adjacent layer thereto.

(Phosphorescent Light-Emitting Dopant)

It is preferable that a phosphorescent light-emitting dopant is incorporated into a light-emitting layer of the organic EL element of the present invention. The phosphorescence wavelength (0-0 band) of the phosphorescent light-emitting dopant is preferably not more than 485 nm, and an ionization potential of the phosphorescent light-emitting dopant is preferably not more than 5.5 eV.

The combination of the phosphorescent light-emitting dopant exhibiting the above-described properties and the compounds represented in the above-mentioned Formulae (1) to (5) of the present invention as a host compound in the light-emitting layer achieved excellent light emission efficiency and extended light emission life.

The phosphorescence 0-0 band is determined by a method described below.

A phosphorescent light-emitting dopant to be measured is dissolved in a mixed solvent of well-deoxygenated ethanol/methanol (4/1 by volume) and placed in a cell for phosphorescence measurement, followed by irradiation of exciting light at a liquid nitrogen temperature of 77 K to measure an emission spectrum 100 ms after completion of the irradiation of exciting light. It is conceivable that since phosphorescence features a longer emission life than fluorescence, most of the light remaining after the 100 ms have elapsed is phosphorescence. Incidentally, a compound exhibiting a phosphorescence life of shorter than 100 ms may be measured by shortening a delay time. However, in cases when shortening the delay time to the extent that the shortened delay time is not distinguished from the life of fluorescence, a problem occurs in that phosphorescence and fluorescence each are indistinguishable, and therefore it is necessary to select an appropriate delay time capable of distinguishing therebetween. For a compound insoluble in the solvent system described above, any appropriate solvent, which can dissolve the compound, may be employed (it is not substantially problematic since a solvent effect on the phosphorescence wavelength in the above measurement method is negligible.).

Subsequently, a method of determining the 0-0 band is described. In the present invention, the 0-0 band is defined as the maximum emission wavelength appearing in the shortest wavelength portion in the phosphorescence spectrum chart obtained via the above measurement method. Since the intensity of a phosphorescence spectrum is generally weak, when the spectrum is magnified, it becomes difficult, in some cases, to distinguish between a noise band and a signal peak. In such a case, it is possible to determine a targeted signal peak in such a manner that a light emission spectrum generated right after irradiation of excitation light (for convenience, referred to as "stationary light spectrum") is magnified, which is then superimposed on another magnified light emission spectrum generated at 100 ms after irradiation of excitation light (for convenience, referred to as "phosphorescence spectrum"), to detect a peak wavelength from the stationary light spectrum originated in the phosphorescence spectrum.

It is also possible to detect a signal peak wavelength by separation of the noise band and the signal peak via a smoothing treatment. The smoothing method by Savitzky and Golay may be applied as the smoothing treatment.

The ionization potential (Ip) of the phosphorescent light-emitting dopant of the present invention is preferably not more than 5.5 eV, and more preferably 4.5 to 5.5 eV. The ionization potential of the present invention is defined as the energy required to emit an electron in the HOMO (highest occupied molecular orbital) level of a compound to a vacuum level, and specifically, it is the energy required to remove an electron from a compound in a state of membrane (a state of layer). The ionization potential can be directly determined via electron spectroscopy. In the present invention, values determined via ESCA 5600, UPS (ultraviolet photoemission spectroscopy), produced by ULVAC-PHI, INC. are used.

Examples of the phosphorescent light-emitting dopant of the present invention exhibiting the 0-0 band of not more than 485 nm are shown, but are not limited to them.

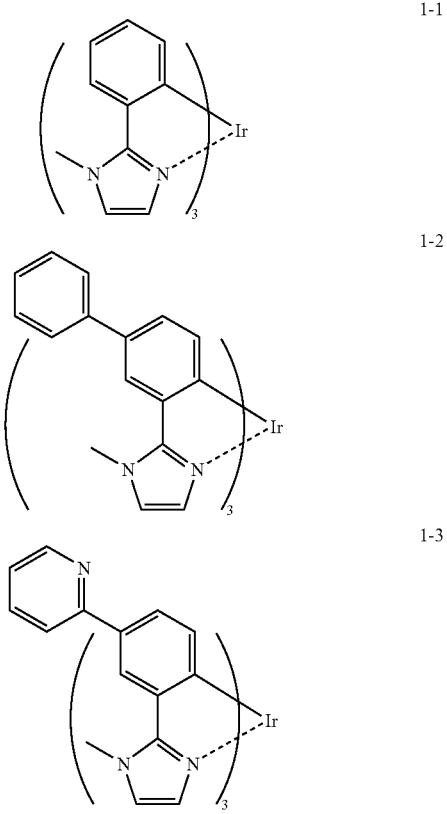

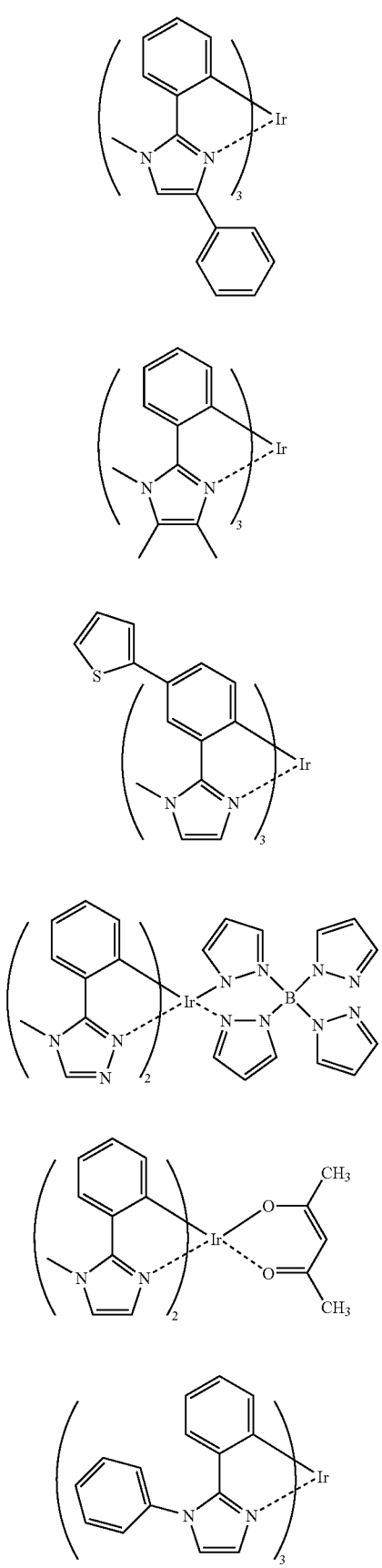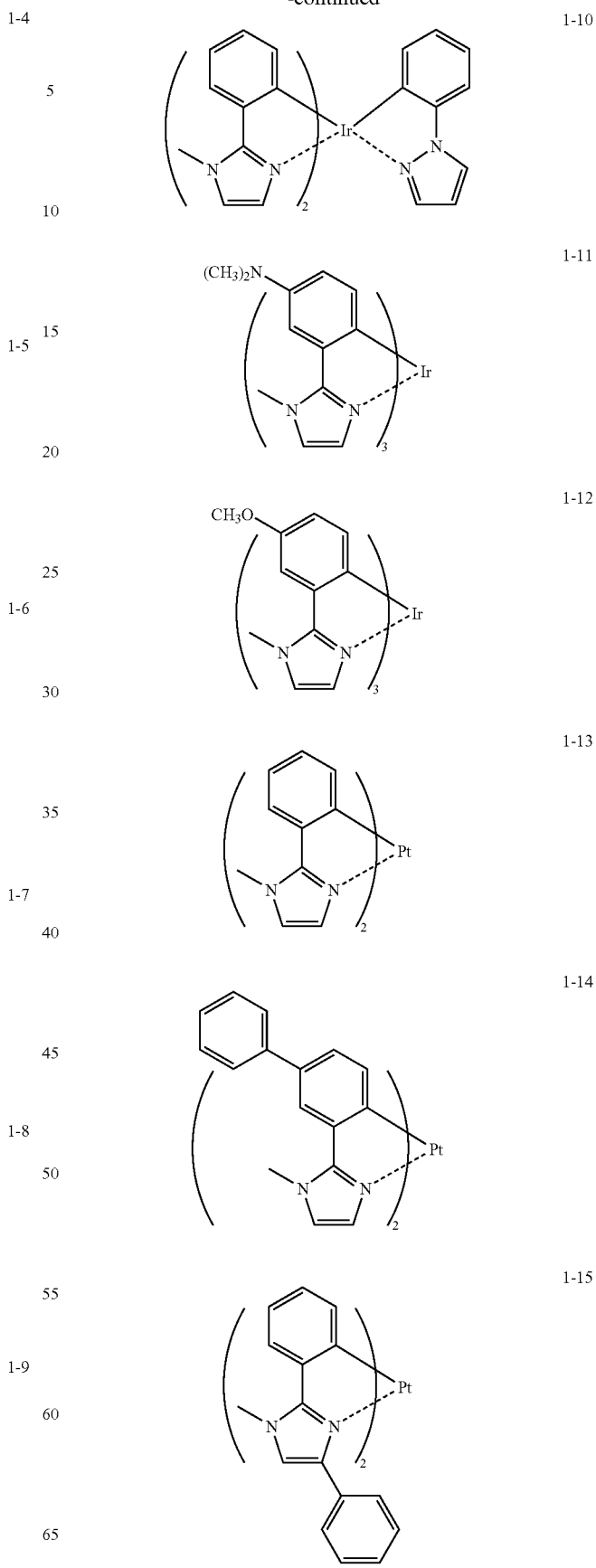

1-16 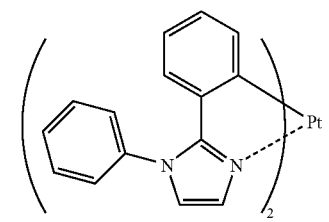
1-17 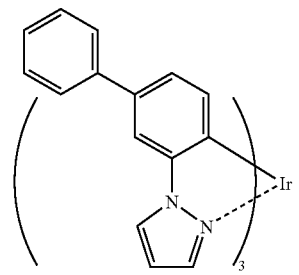
1-18 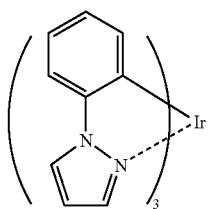
1-19 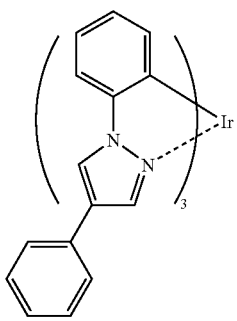
1-20 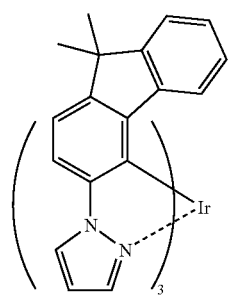
1-21 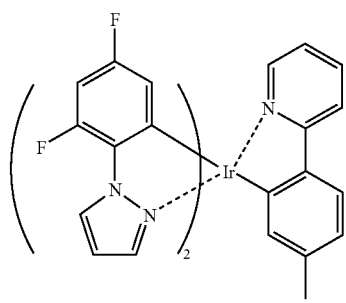
1-22 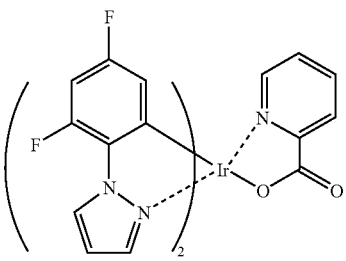
1-23 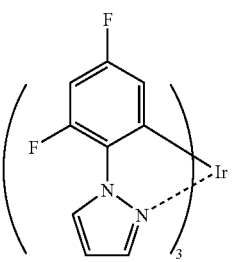
1-24 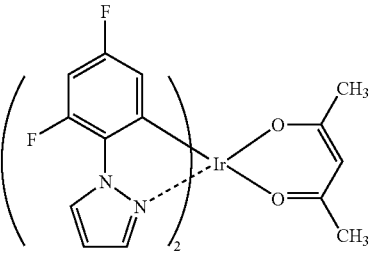
1-25 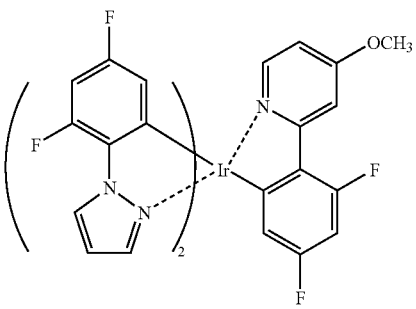
1-26 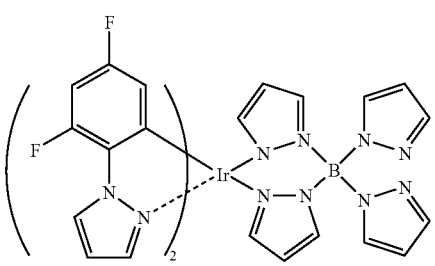
1-27 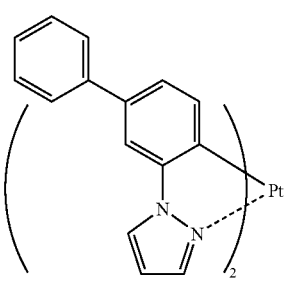

1-28 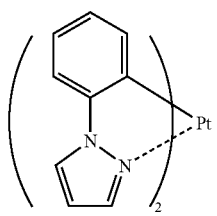
1-29 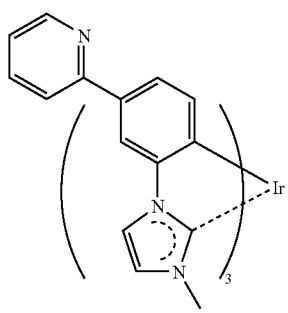
1-30
1-31
1-32
1-33 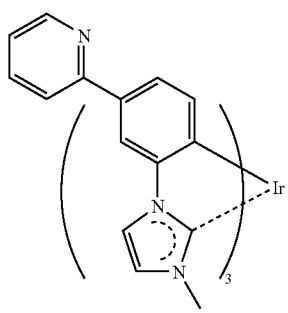
1-34
1-35 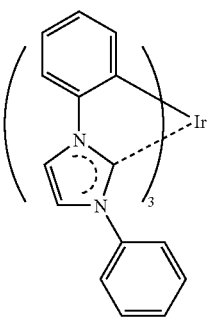
1-36 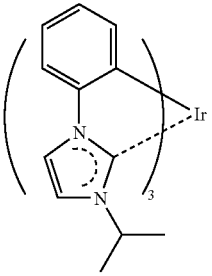
1-37 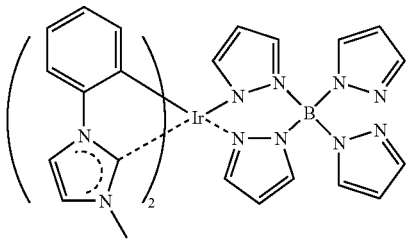

1-38
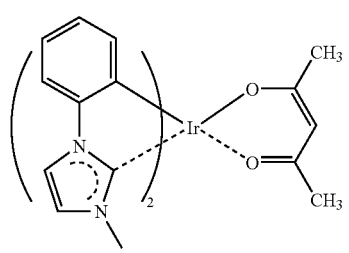
1-39
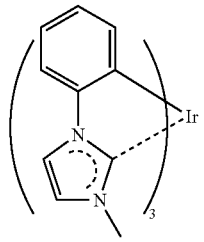
1-40
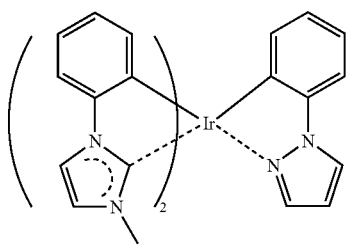
1-41
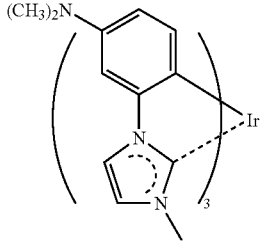
1-42
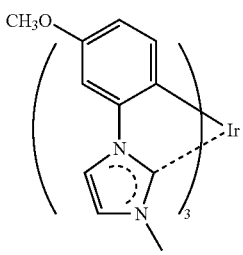
1-43
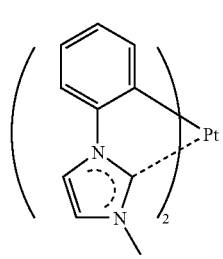
1-44
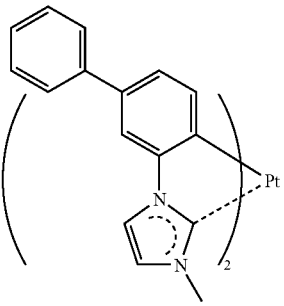
1-45
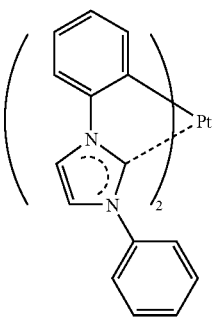
1-46
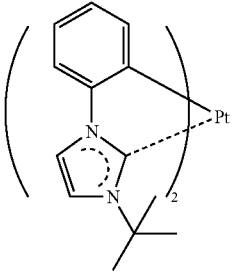
1-47
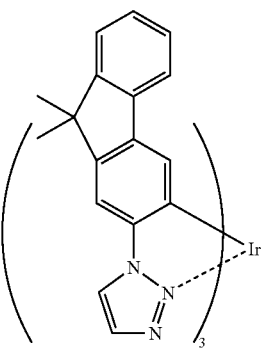
1-48
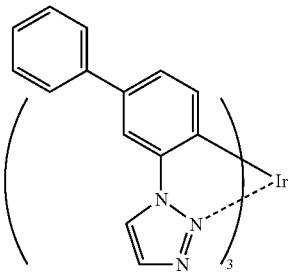

1-49
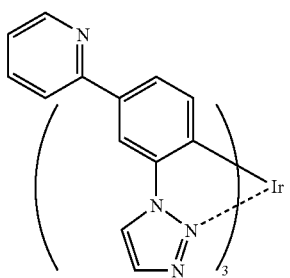
1-50
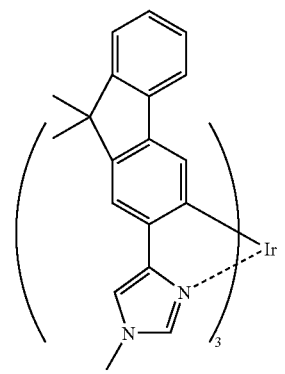
1-51
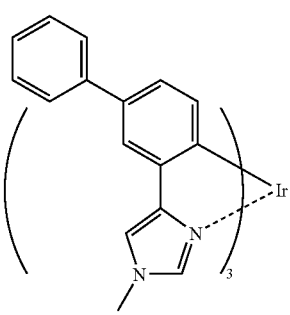
1-52
1-53
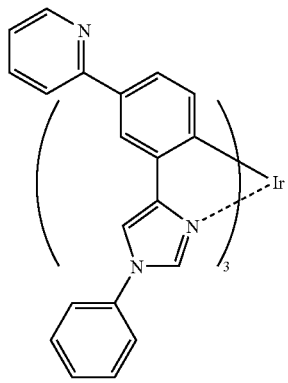
1-54
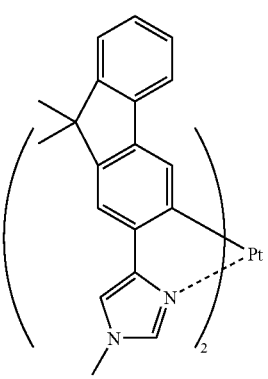
1-55
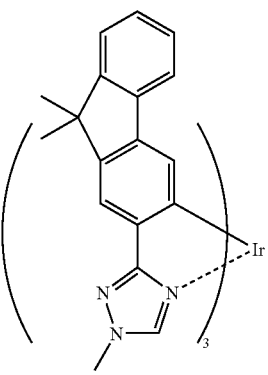
1-56
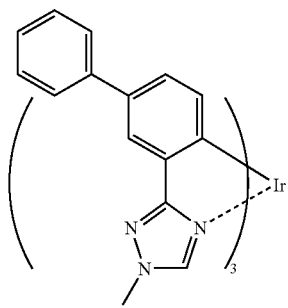

1-57 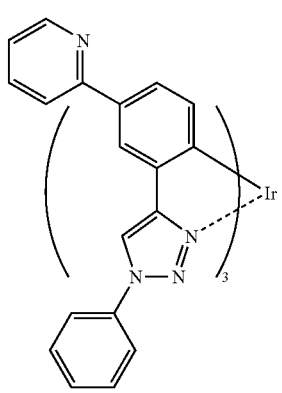
1-58 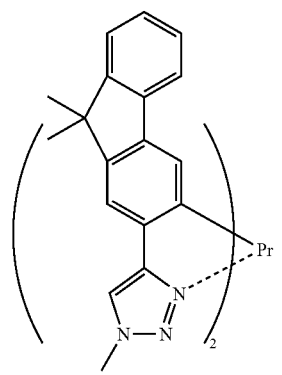
1-59 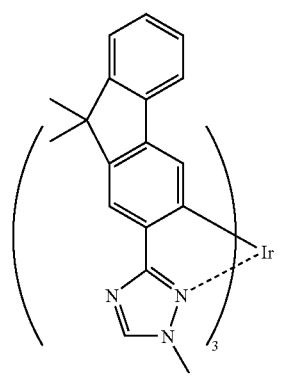
1-60 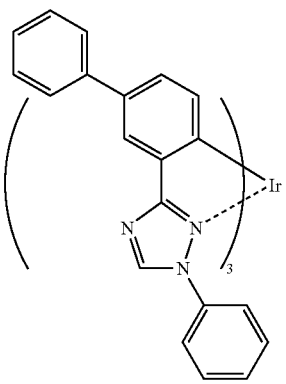
1-61 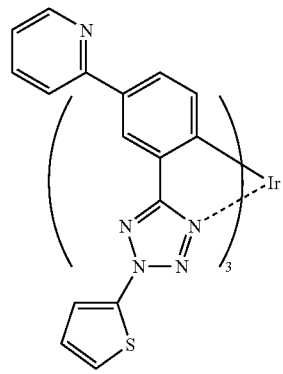
1-62 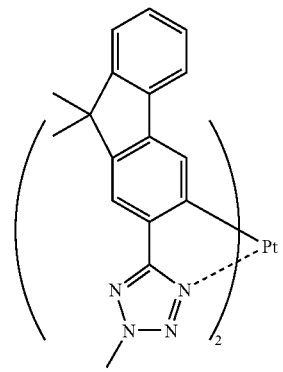
1-63 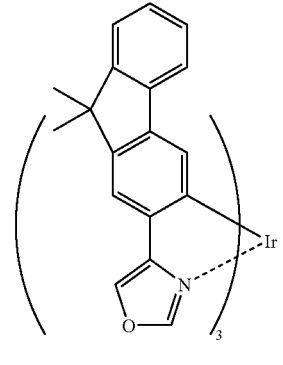
1-64 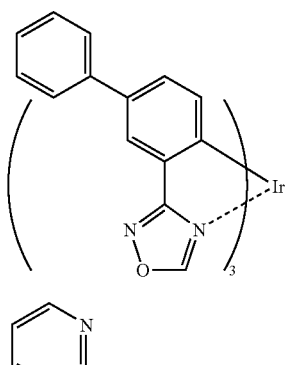
1-65 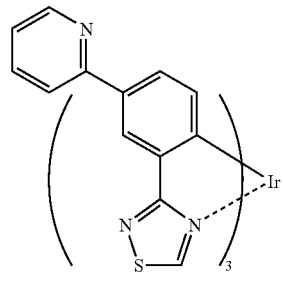

1-66 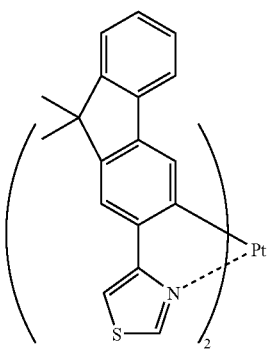
1-67 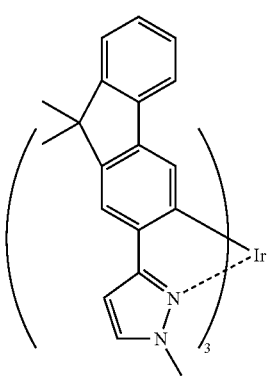
1-68 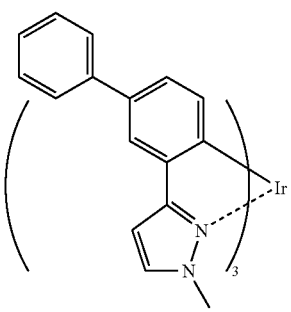
1-69 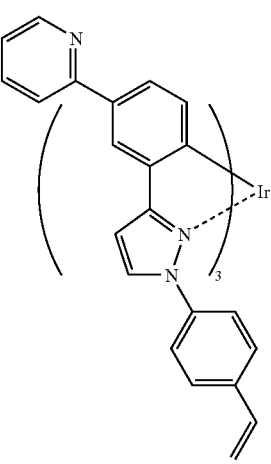
1-70 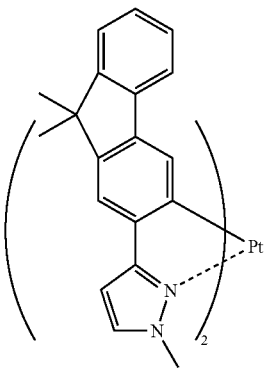
1-71 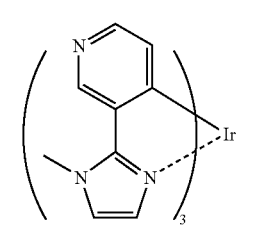
1-72 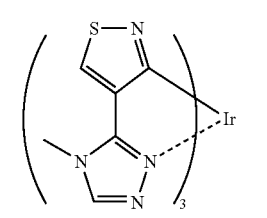
1-73 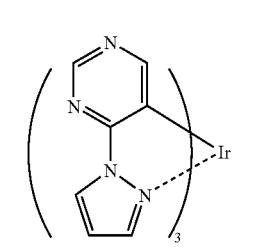
1-74 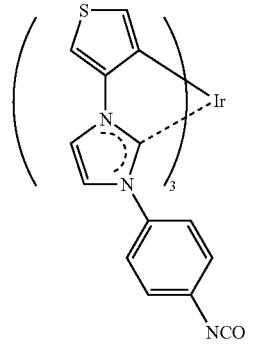
The specific examples of the phosphorescent light-emitting dopant other than the blue light-emitting phosphorescent light-emitting dopant are shown below.

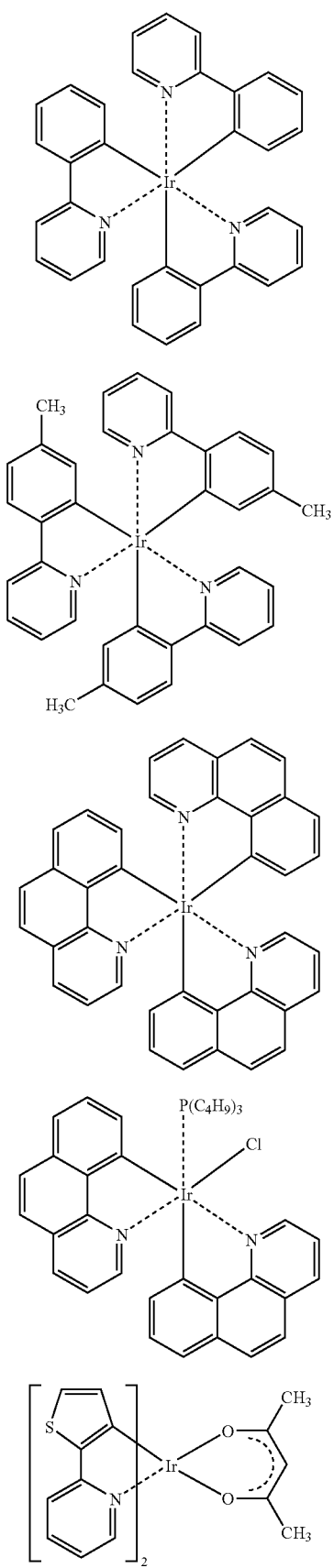

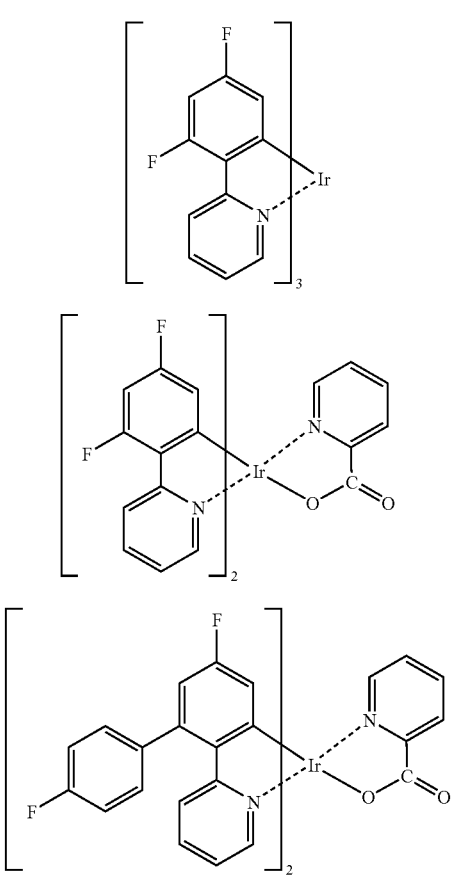

Such phosphorescent light-emitting dopants can be synthesized by applying a method described in documents such as Organic Letter, vol. 3, No. 16, pp. 2579-2581 (2001), Inorganic Chemistry vol. 30, No. 8, pp. 1685-1687 (1991), J. Am. Chem. Soc., vol. 123, p. 4304 (2001), Inorganic Chemistry vol. 40, No. 7, pp. 1704-1711 (2001), Inorganic Chemistry vol. 41, No. 12, pp. 3055-3066 (2002), New Journal of Chemistry, vol. 26, p. 1171 (2002), and reference documents described in these documents.

The host compounds in the light-emitting layer represented by the above-described Formulae (1) to (5) of the present invention are preferably employed, but commonly known host compounds may also be employed. The above compounds may be employed in combinations thereof.

The host compound of the present invention is defined as a compound whose mass ratio is not less than 20% of the whole compounds in the light-emitting layer, and exhibits a phosphorescence quantum yield of phosphorescent light emission of less than 0.1. The phosphorescence quantum yield is preferably less than 0.01.

Further, a plurality of commonly known host compounds may be used in combination. It is possible to control charge transfer by employing a plurality of host compounds, to enable the organic EL element to be highly efficient. Also it is possible to mix different emitted lights by employing a plurality of compounds represented by Formulae (1) to (5) of the present invention, to result in optional colors of emitted light. Controlling a kind of light emitting metal complex and an amount of dope enables white light emission, to result in applications for illumination and back lighting.

As commonly known host compounds which may be used in combination, preferred are compounds which prevent elongation of wavelength of emitted light, and further exhibit high Tg (glass transition temperature), as well as exhibiting positive hole transporting capability and electron transporting capability.

Specific examples of the light-emitting host include, but are not limited to, compounds described in the following.

Patent Documents; JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2602-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, and 2002-308837.

In the present invention, in case of having a plurality of light emitting layers, it is preferable that at least 50% of the total amount of host compounds in the aforesaid layers is an identical compound to readily provide a uniform film state over the whole organic layer, and further, it is more preferable that phosphorescent light-emitting energy of the aforesaid compound is not less than 2.9 eV, since it is advantageous in efficiently restraining energy transfer from dopant, and obtaining high brightness.

The phosphorescent light-emitting energy in the present invention denotes the peak energy of 0-0 band of the phosphorescent light emission which is provided by measurement of photoluminescence of a vapor deposited film having 100 nm of a host compound on a substrate.

The light emitting principle of phosphorescence emitting metal complexes is of two types; one is an energy transfer type in which carriers undergo recombination on the host compounds to which carriers are transported to generate an excited state of the host compounds and by transferring the resulting energy to phosphorescence emitting complexes, light emission is obtained, and the other is a carrier trap type in which phosphorescence emitting metal complexes work as a carrier trap and carriers undergo recombination on the phosphorescence emitting metal complexes, whereby it is possible to obtain light emission from the phosphorescence emitting metal complexes. In either case, an essential condition is that energy of the excited state of phosphorescence emitting metal complexes is lower than that of the excited state of host compounds.

In the present invention, the maximum wavelength of phosphorescence emitted by phosphorescence emitting organic metal complexes is not particularly limited. In principle, it is possible to change the wavelength of emitted light by appropriately selecting the central metal, the ligand, and the substituent of the ligand.

Color of light emitted from the organic EL elements of the present invention and the compounds according to the present invention is specified in such a manner that results determined by spectroradiometric luminance meter CS-1000 (produced by Konica Minolta Sensing Inc.) are applied to the CIE chromaticity coordinates in Figs. 4.16 on page 108 of "Shinpen Shikisai Kagaku Handbook (New Edition Color Science Handbook")" (edited by The Color Science Association of Japan, University of Tokyo Press, 1985).

"White element", as described in the present invention, means that when front luminance of a viewing angle of 2° C. is determined via the above method, chromaticity in the CIE 1931 Chromaticity System at 1,000 $Cd/m^2$ is in the range of $X=0.33\pm0.07$ and $Y=0.33\pm0.07$.

It is possible to form the light emitting layer in such a manner that the above compounds are modified to a film employing the conventional thin film producing methods such as a vacuum deposition method, a spin coating method, a casting method, an LB method, or an ink-jet method.

In the present invention, the light emitting layer incorporates layers which differ in spectra of the emitted light so that the wavelength of each maximum emitted light is in the range of 430-480 nm, 510-550 nm and 600-640 nm, or a layer composed of the those laminated layers.

Laminated layer order in the light emitting layer is not particularly limited, and a non-light emitting interlayer may be provided between the light emitting layers. In the present invention, it is preferable that of all light emitting layers, at least one blue light emitting layer is provided in the position which is nearest to the anode.

Further, when at least four light emitting layers are arranged, in order to enhance luminance stability, it is preferable to laminate layers in the anode-near order of blue, green, and red, such as blue/green/red/blue, blue/green/red/blue/green, or blue/green/red/blue/green/red.

The total thickness of light emitting layers is not particularly limited. The above thickness is selected to be in the range of 2 nm-5 µm, but to be preferably in the range of 2-200 nm. In the present invention, the thickness is most preferably in the range of 10-20 nm. When the layer is excessively thin, it is difficult to obtain uniformity of the film. On the contrary, when the film is thicker than the above range, high voltage is undesirably required to obtain light emission. It is preferable that the film thickness of not more than 20 nm exhibits an effect of improving stability of emitted light colors against fluctuations of driving current, as well as an advantage with respect to voltage.

Thickness of each light emitting layer is selected to be preferably in the range of 2-100 nm, but to be more preferably in the range of 2-20 nm. The relationship of thickness of each of the blue, green, and red light emitting layer is not particularly limited. However, it is preferable that of the three light emitting layers, the blue light emitting layer is thickest (in the case of presence of a plurality of blue layers, the total thickness).

Further, a plurality of light emitting compounds may be blended in each light emitting layer in a range in which the above emission maximum wavelength is maintained. For example, blended in the blue light emitting layer may be blue light emitting compounds exhibiting a maximum emission wavelength of 430-480 nm and green light emitting compounds exhibiting a maximum emission wavelength of 510-550 nm.

<Positive Hole Transport Layer>

A positive hole transport layer contains a material having a function of transporting a positive hole, and in a broad meaning, a positive hole injection layer and an electron inhibition layer are also included in a positive hole transport layer. A single layer of or plural layers of a positive hole transport layer may be provided.

A positive hole transport material is those having any one of a property to inject or transport a positive hole or a barrier property to an electron, and may be either an organic substance or an inorganic substance. For example, listed are a triazole derivative, an oxadiazole derivative, an imidazole derivative, a polyallylalkane derivative, a pyrazolone derivative, a phenylenediamine derivative, an allylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive polymer oligomer and specifically preferably such as thiophene oligomer.

As a positive hole transport material, those described above can be utilized, however, it is preferable to utilized a porphyrin compound, an aromatic tertiary amine compound and a styrylamine compound, and specifically preferably an aromatic tertiary amine compound.

Typical examples of an aromatic tertiary amine compound and a styrylamine compound include N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl 4,4'-diaminobiphenyl; 1,1-bis(4-di-p-tolylaminophenyl)-4-phenylcyclohexane; bis(4-dimethylamino-2-methyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminophenylether; 4,4'-bis(diphenylamino)quarterphenyl; N,N,N-tri(p-tolyl)amine; 4-(di-p-tolylamino)-4'-[4-(di-p-triamino)styryl]stilbene; 4-N,N-diphenylamino-(2-diphenylvinyl)benzene; 3-methoxy-4'-N,N-diphenylaminostilbene; and N-phenylcarbazole, in addition to those having two condensed aromatic rings in a molecule described in U.S. Pat. No. 8,061,569, such as 4,4'-bis[N-(1-naphthyl)-N-phenylamino]biphenyl (NDP), and 4,4',4''-tris[N-(3-methylphenyl)-N-phenylamino]triphenylamine (MDTDATA), in which three of triphenylamine units are bonded in a star burst form, described in JP-A 4-308688.

Polymer materials, in which these materials are introduced in a polymer chain or constitute the main chain of polymer, can be also utilized.

Further, an inorganic compound such as a p type-Si and a p type-SiC can be utilized as a positive hole injection material and a positive hole transport material.

Further, it is possible to employ so-called p-type positive hole transporting materials which are described in JP-A No. 11-251067 and J. Huang et al., report (Applied Physics Letters 80 (2002). P. 139). In the present invention, since it is possible to prepare a more efficient light emitting element, it is preferable to employ these materials.

This positive hole transport layer can be prepared by forming a thin layer made of the above-described positive hole transport material according to a method well known in the art such as a vacuum evaporation method, a spin coating method, a cast method, an inkjet method and a LB method. The layer thickness of a positive hole transport layer is not specifically limited, however, is generally 5 nm-5 µm, preferably 5 nm 200 nm. This positive transport layer may have a single layer structure comprised of one or not less than two types of the above described materials.

Further, it is possible to employ an impurity-doped positive hole transporting layer exhibiting high "p" property. As such examples, listed are those described in each of JP-A Nos. 4-297076, 2000-196140, and 2001-102175, as well as J. Appl. Phys., 95, 5773 (2004).

In the present invention, it is preferable to employ such a positive hole transporting layer exhibiting high "p" property, since it is possible to prepare an element which results in low electrical power consumption.

<Electron Transport Layer>

An electron transfer layer is composed of a material having a function to transfer an electron, and an electron injection layer and a positive hole inhibition layer are included in an electron transfer layer in a broad meaning. A single layer or plural layers of an electron transfer layer may be provided.

Heretofore, when an electron transfer layer is single layer or a plurality of layers, an electron transfer material (combined with a hole inhibition material) utilized in an electron transfer layer adjacent to a cathode side against an emission layer is provided with a function to transmit an electron injected from a cathode to an emission layer, and compounds conventionally well known in the art can be utilized by arbitrarily selection as a material thereof. Examples of a material utilized in this electron transfer layer include such as a nitro-substituted fluorene derivative, a diphenylquinone derivative, a thiopyradineoxide derivative, carbodiimide, a fluorenylidenemethane derivative, anthraquinonedimethane, anthrone derivatives, and an oxadiazole derivative. Further, a thiazole derivative in which an oxygen atom in the oxadiazole ring of the above-described oxadiazole derivative is substituted by a sulfur atom, and a quinoxaline derivative having a quinoxaline ring which is known as an electron attracting group can be utilized as an electron transfer material. Polymer materials, in which these materials are introduced in a polymer chain or these materials form the main chain of polymer, can be also utilized.

Further, a metal complex of a 8-quinolinol derivative such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(S-methyl-8-quinolinol)aluminum and bis(8-quinolinol) zinc (Znq); and metal complexes in which a central metal of the aforesaid metal complexes is substituted by In, Mg, Cu, Ca, Sn, Ga or Pb, can be also utilized as an electron transfer material. Further, metal-free or metal phthalocyanine, or those the terminal of which is substituted by an alkyl group and a sulfonic acid group, can be preferably utilized as an electron transfer material. Further, distyrylpyrazine derivative, which has been exemplified as a material of an emission layer, can be also utilized as an electron transfer material, and, similarly to the case of a positive hole injection layer and a positive hole transfer layer, an inorganic semiconductor such as an n-type-Si and an n-type-SiC can be also utilized as an electron transfer material.

This electron transport layer can be prepared by forming a thin layer made of the above-described electron transport material according to a method well known in the art such as a vacuum evaporation method, a spin coating method, a cast method, an inkjet method and a LB method. The layer thickness of an electron transport layer is not specifically limited; however, is generally 5 nm-5 μm, preferably 5 nm-200 nm. This electron transport layer may have a single layer structure comprised of one or not less than two types of the above described materials.

Further, it is possible to employ an impurity-doped electron transporting layer exhibiting high "n" property. Examples thereof include those described in JP-A No. 4-297076, 10-270172, 2000-196140, and 2001-102175, as well as J. Appl. Phys., 95, 5773 (2004).

In the present invention, it is preferable to employ such an electron transporting layer exhibiting high "n" property, since it is possible to prepare an element winch results in low electrical power consumption.

<Substrate>

A substrate (also referred to as Base Plate, Base Material or Support) according to an organic EL element of the present invention is not specifically limited with respect to types of such as glass and plastics provided being transparent, however, a substrate preferably utilized includes such as glass, quartz and transparent resin film. A specifically preferable substrate is resin film capable of providing an organic EL element with a flexible property.

Resin film includes such as film comprised of a polyester such as polyethylene terephthalate (PET) and polyethylene naphthalate (PEN); polyethylene, polypropyrene, a cellulose ester or a cellulose ester derivative such as cellophane, cellulose diacetate, cellulose triacetate, cellulose acetate butylate, cellulose acetate propionate (CAP), cellulose acetate phtalate (TAC), cellulose nitrate; poly vinylidene chloride, polyvinyl alcohol, polyethylene vinylalcohol, syndiotactic polystyrene, polycarbonate, norbornene resin, polymethyl pentene, polyether ketone, polyimide, polyether sulphone (PES), polyphenylene sulfide, polysulphones, polyether imide, polyether ketone imide, poly amide, fluorine contained resin, nylon, polymethylmethacrylate, acrylates or polyacrylates, ARTON (Product by JSR Corporation), and cyclo olefin resin such as APEL(Product name by Mitsui Chemicals, Inc).

On the surface of resin film, an inorganic or organic cover layer or a hybrid cover layer comprising the both may be formed, and the film is preferably provided with a high barrier ability. A preferably barrier film has a moisture permeability of not more than 0.01 g/(m$^2$·24 hr) at a temperature of 25±0.5° C., relative humidity (90±2)% RH, measured based on JIS K 7129-1992, and more preferably an oxygen permeability of not more than 1×10$^{-3}$ ml/(m$^2$·24 hr·MPa) measured based on JIS K 7126-1987 and a moisture permeability of not more than 1×10$^{-5}$ g/(m$^2$·24 hr).

As barrier film forming materials, employed may be those which function to retard invasion of materials, such as moisture or oxygen, which deteriorate the element. It is possible to employ, for example, silicon oxide, silicon dioxide and silicon nitride. Further, to improve brittleness of the above film, it is preferable to result in a laminated layer structure composed of these inorganic layers and organic materials. The order of laminated inorganic layers and organic layers is not particularly limited, but it is preferable that both are alternately laminated several times.

Forming methods of barrier films are not particularly limited, and it is possible to employ, for example, a vacuum deposition method, a sputtering method, a reactive sputtering method, a molecular beam epitaxy method, a cluster ion beam method, an ion plating method, a plasma polymerizing method, an atmospheric pressure plasma polymerizing method, a plasma CVD method, a laser CVD method, a thermal CVD method, and a coating method. The atmospheric pressure plasma polymerizing method, described in JP-A No. 2004-68143, is particularly preferred.

Examples of opaque substrates include metal plates composed of aluminum or stainless steel, films, opaque resin substrates, and ceramic substrates.

The taking out efficiency of emission of an organic EL element of this invention at room temperature is preferably not less than 1% and more preferably not less than 2%. Herein, taking out quantum efficiency (%)=photon number emitted out of organic EL element/electron number flown into organic EL element×100.

Further, a hue improving filter such as a color filter may be utilized in combination. In the case of an illumination application, roughening processed film (such as anti-glare film) can be also utilized in combination to decrease emission unevenness.

<<Sealing>>

An example of a sealing method employed in the present invention may include a method in which a sealing member and an electrode, or a substrate are adhered via adhesive agents.

The sealing member may be arranged to cover the display portion of an organic EL element, and may be either a concave plate or a flat plate. Further, its transparency and electric insulation are of no particular concern.

Specifically listed are glass plates, polymer plate-films, and metal plate-films. Glass plates may specifically include soda lime glass, barium-strontium containing glass, lead glass, aluminosilicic acid glass, boron silicic acid glass, barium silicic acid glass, and quartz glass. Further, listed as polymer plates may be those composed of polycarbonate, acryl, polyethylene terephthalate, polyether sulfide, and polysulfone. Metal plates include those composed of at least one selected from the group consisting of stainless steel, iron, copper, aluminum, magnesium, nickel, zinc, chromium, titanium, molybdenum, silicon, germanium, and tantalum.

In the present invention, in view of the capability of modifying an element to a thin film, it is preferable to employ polymer films and metal films. Furthermore, it is preferable that the polymer films exhibit an oxygen permeability of at most $1\times10^{-3}$ ml/(m$^2\cdot$24 hours$\cdot$MPa), determined by the method based on JIS K 7126-1987, and a moisture permeability (at $25\pm0.5°$ C. and relative humidity of $90\pm2\%$) of $10^{-3}$ g/(m$^2\cdot$24 hours), determined by the method based on JIS K 7129-1992.

In order to form concave modify sealing members, employed are a sand blasting process or a chemical etching process.

Specific adhesive agents may include photocurable and thermally curable type adhesive agents having a reactive vinyl group of acrylic acid oligomers and methacrylic acid oligomers, as well as moisture curable type adhesive agents such as 2-cyanoacrylic acid esters. Further listed may be thermally and chemically curable types (being a two-liquid mixture) such as epoxy based ones. Further listed may be hot-melt type polyamides, polyesters, and polyolefin. Still further listed may be cationically curable type ultraviolet ray curable type epoxy resin adhesive agents.

Since organic EL elements occasionally deteriorate due to thermal processing, preferred are those which enable adhesion curing between room temperature and 80° C. Further, desiccating agents may be dispersed into the above adhesive agents. Adhesive agents may be applied to sealing portions employing a commercial dispenser, or may be printed in the same manner as screen printing.

Further, it is appropriate to prepare a sealing film by forming inorganic material and organic material layers which come into contact with a substrate in such a manner that on the exterior of an electrode which interposes an organic layer and faces the substrate, the above electrode and an organic layer are thereby covered. In such case, materials to form the above film may be employable as long as they retard invasion of those, such as moisture or oxygen, which result in deterioration of the elements. For example, employed may be silicon oxide, silicon dioxide, or silicon nitride. Further, in order to minimize brittleness of the above film, it is preferable to form a laminated layer structure composed of these inorganic layers and layers composed of organic materials. Formation methods of these films are not particularly limited, and examples thereof may include a vacuum deposition method, a sputtering method, a reactive sputtering method, a molecular beam epitaxy method, a cluster ion beam method, an ion plating method, a plasma polymerizing method, an atmospheric pressure plasma polymerizing method, a plasma CVD method, a laser CVD method, a thermal CVD method, and a coating method.

It is preferable that in a gas or liquid phase, inert gases such as nitrogen or argon, or inert liquids such as fluorinated hydrocarbon or silicone oil are injected into the space between the sealing member and the display region. Further, it is possible to form vacuum. Still further, it is possible to enclose hygroscopic compounds in the interior.

Examples of hygroscopic compounds include metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); and perchlorates (for example, barium perchlorate and magnesium perchlorate). Of the sulfates, metal halides, and perchlorates, anhydrous salts thereof are appropriately employed.

<<Protective Films and Protective Plates>>

In order to enhance mechanical strength of elements, a protective film or plate may be arranged on the exterior of the above sealing film which interposes the organic layer and faces the substrate or the above sealing film. Specifically, when sealing is carried out via the above sealing film, its mechanical strength is not always sufficient. Consequently, it is preferable to arrange such a protective film or plate. Employable materials include glass plate, polymer plate-film, and metal plate-film which are the same as those employed for the above sealing. In view of light weight and capability of forming a thin film, it is preferable to employ a polymer film.

<<Light Taking-Out>>

It is generally stated that with regard to an organic EL element, light is generated in the interior of the layer of a higher refractive index (a refractive index of 1.7-2.1) than that of air and of light generated in the light emitting layer, only about 15% to about 20% of the light is taken out. The reasons are that light which is incident to the interface (the interface between the transparent substrate and air) at angle θ, which is greater than the critical angle, is not taken out of the element due to total reflection, while all light is reflected between the transparent electrode or the light emitting layer and the transparent substrate, and light is channeled to the transparent electrode or the light emitting layer, whereby light escapes to the element side direction.

Examples of methods to enhance the light taking-out efficiency include: a method in which asperity is formed on the surface of a transparent substrate and total reflection at the interface between the transparent substrate and air is minimized (U.S. Pat. No. 4,774,435), a method in which a light collecting substrate is used (JP-A No. 63-314795), a method in which a reflective surface is formed on the side surface of an element (JP-A No. 1-220394), a method in which a flat layer of an intermediate refractive index is introduced between a substrate and a light emitting body, whereby an antireflective film is formed (JP-A No. 62-172691), a method in which between a substrate and a light emitting body introduced is a flat layer of a refractive index which is lower than that of the above substrate (JP-A No. 2001-202827), and a method in which diffraction gratings are formed between any of a substrate, a transparent electrode layer, and a light emitting layer (including between a substrate and an exterior) (JP-A No. 11-283751).

In the present invention, it is possible to employ any of the above methods in combination with the organic EL element of the present invention, and it is possible to appropriately employ the method which introduces a flat layer of a refractive index which is lower than that of the substrate between the above substrate and the light emitting body, or the method in which diffraction gratings are formed between the substrate and either the transparent electrode layer or the light emitting layer (including between the substrate and the exterior).

In the present invention, by combining these methods, it is possible to prepare an element which exhibits higher luminance or higher durability.

When a medium of a low refractive index is formed at a thickness which is greater than the light wavelength between the transparent electrode and the transparent substrate, taking-out efficiency of light emitted from the transparent electrode increases as the refractive index of the medium decreases.

Examples of layers of a low refractive index include aerogels, porous silica, magnesium fluoride, and fluorine based polymers. Since the refractive index of the transparent substrate is commonly about 1.5 about 1.7, the refractive index of low refractive index layers is preferably at most about 1.5, but is more preferably at most 1.35.

Further, the thickness of low refractive index media is preferably at least twice, the wavelength in media. The reason for this is that the thickness of low refractive index media roughly approaches the light wavelength so that electromagnetic wave permeated via evanescent enters the substrate, whereby effects of the low refractive index layer are decreased.

The method which employs an interface which results in total reflection or introduces diffraction gratings into media exhibits features which result in a high effect to enhance light taking-out efficiency. These methods are achieved as follows. By utilizing properties of the so-called Bragg diffraction in which diffraction gratings result in primary diffraction and secondary diffraction so that it is possible to change light direction to the specified direction which is different from the diffraction, of light generated from the light emitting layer, light which is not able to going out due to the total reflection between the layers is diffracted at the interface between any layers or by introducing diffraction gratings into media (within the transparent substrate or within the transparent electrode), whereby light is introduced into the exterior.

It is preferable that the introduced diffraction gratings exhibit two-dimensional cyclic refractive indices. The reason is that since the light emitting layer randomly emits light in all directions, a common one-dimensional diffraction grating, which carries a cyclic refractive index distribution only in a certain direction, diffracts light only in the specified direction, whereby light taking-out efficiency is not so enhanced. However, by changing the refractive index distribution to a two-dimensional distribution, light is diffracted in all directions to enhance the light taking-out efficiency.

As noted above, the diffraction grating may be positioned at the interface between any layers or in a medium (in a transparent substrate or a transparent electrode), but is preferably positioned adjacent to the organic light emitting layer where the light is generated.

At the time, the cycle of the diffraction grating is preferably by a factor of about ½ to about 3 of the light wavelength in the medium.

It is preferable that the arrangement of detraction gratings is two-dimensionally repeated to result in a square lattice, a triangular lattice or a honeycomb lattice.

<<Light Collecting Sheet>>

With regard to the organic EL element of the present invention, it is possible, for example, to enhance luminance in a specified direction by collecting light in a specified direction such as toward the front with respect to the light emitting element surface by forming a micro-lens array structure or by combining it with a so-called light-collecting sheet.

The micro-lens array is, for example, formed in such a manner that quadrangular pyramids of a side length of 30 µm and an apex angle of 90 degrees are two-dimensionally arranged on the light taking-out side of a substrate. The side length is preferably 10-100 µm. When the length is less then the lower limit, diffraction effects occur to result in coloring, while when it is more than the upper limit, the undesirable thickness results.

It is possible to employ, as the light collecting sheet, ones which are commercially employed, for example, as in LED backlights of liquid crystal display devices. It is possible, for example, to employ, as such sheets, luminance enhancing film (BEF), produced by Sumitomo 3M Ltd. Examples of the shape of the prism sheet may include ones in which Δ shaped stripes of an apex angle of 90 degrees and a pitch of 50 µm are formed on a substrate and the others such as a shape in which the apex angle is rounded, a shape in which the pitch is randomly changed or other appropriate shapes.

Further, in order to control the light radiation angle from the light emitting element, a light diffusing plate-film may be simultaneously employed with a light collecting sheet. For example, it is possible to employ the diffusion film (LIHGT-UP) produced by Kimoto Co., Ltd.

<Preparation Method of Organic EL Element>

As an example of a preparation method of an organic EL element described in the present invention, a preparation method of an organic EL element, comprising anode/positive hole injection layer/positive hole transport layer/emission layer/electron transport layer/electron injection layer/cathode, will be explained.

First, on an appropriate substrate, a thin layer comprising a desired electrode substance such as an anode electrode substance is formed by means of evaporation or spattering so as to make a layer thickness of not more than 1 µm and preferably of 10-200 nm, whereby an anode is prepared.

Next, on this layer, thin layers containing organic substances of such as a positive hole injection layer, a positive hole transport layer, an emission layer, a positive hole inhibition layer and an electron transport layer are formed.

A thin layer forming method of these layers containing the organic substances includes an evaporation method and a wet process (such as a spin coat method, a cast method, an inkjet method, and a printing method) as described before. According to the present invention, a spin coat method, an inkjet method, and a printing method is specifically preferable with respect to easy preparation of a homogeneous layer and bare generation of pinholes.

In the present invention, during formation of a light emitting layer, it is preferable that a film is prepared via a coating method employing a liquid composition in which the organic metal complexes of Formula (1)-(5) according to the present invention are dissolved or dispersed, and the coating method is preferably the ink-jet method.

As liquid media in which the organic metal complexes of Formula (1)-(5) according to the present invention are dissolved or dispersed, employed may, for example, be ketones such as methyl ethyl ketone or cyclohexanone; aliphatic acid esters such as ethyl acetate; halogenated hydrocarbons such as dichlorobenzene; and organic solvents such as DMF or DMSO. Further, it is possible to achieve dispersion via dispersing methods employing ultrasonic waves, high shearing force dispersion, or media dispersion.

After forming these layers, in order to form a cathode, a thin layer of at most 1 µm, composed of cathode compounds, is applied onto the above layers to result in a layer thickness in the range of 50-200 nm via a vapor deposition or sputtering method, whereby a desired organic EL element is prepared.

Further, by reversing the preparation order, it is possible to achieve preparation, in the order of a cathode, an electron injecting layer, an electron transporting layer, a positive hole transporting layer, a positive hole injecting layer, and an anode. When direct electric current voltage is applied to the multicolor display device prepared as above, application of voltages of 2-40 V, employing the anode as + and the cathode as −, makes it possible to observe light emission. Further, alternating current voltage may be applied, and the waveform of the applied alternating electric current is not limited.

<<Application>>

It is possible to employ the organic EL element of the present invention as various light emitting light sources. Examples of such light emitting light sources include, but are not limited to, home illumination, car interior illumination, backlights for watches and liquid crystals, advertising displays, signals, light sources for optical memory media, light sources for electrophotographic copiers, light sources for optical communication processors, and light sources for optical sensors. Of these, it is possible to effectively employ the above EL element for use as a backlight of liquid crystal display devices and light sources for illumination.

If desired, the organic EL element of the present invention may be subjected during film production to patterning via a metal masking or ink-jet printing method. When the above patterning is carried out, only the electrode may be subjected to patterning, the electrode and the light emitting layer may be subjected to patterning, or all layers of the element may be subjected to the above patterning.

EXAMPLES

The present invention is described below with reference to examples, but the embodiment of the invention is not limited to them.

Example 1

Preparation of Organic EL Elements 1-1

A pattern was formed on a substrate composed of a glass plate of 100 mm×100 mm×1.1 mm and a 100 nm ITO (indium tin oxide) layer (NA45: manufactured by NH Technoglass Co., Ltd.) as an anode. Then the resulting transparent substrate, having the above ITO transparent electrode, was subjected to ultrasonic cleaning in iso-propylalcohol, dried with a dry nitrogen gas, and then subjected to UV-ozone cleaning for 5 minutes. Thus obtained transparent substrate was fixed to a substrate holder of a commercially available vacuum deposition apparatus. Further, 200 mg of α-NPD was placed in a first resistive heating molybdenum boat, 200 mg of CBP, as a host compound, was placed in a second resistive heating molybdenum boat, 200 mg of BCP was placed in a third resistive heating molybdenum boat, 100 mg of illustrated compound 1-1 was placed in a fourth resistive heating molybdenum boat, and 200 mg of Alq$_3$ was placed in a fifth resistive heating molybdenum boat, and the resulting boats were fixed in the vacuum deposition apparatus.

After the pressure in the vacuum tank was reduced to 4×10$^{-4}$ Pa, the above heating boat carrying α-NPD was heated by applying an electric current to evaporate α-NPD onto the transparent substrate at a deposition rate of 0.1 nm/sec to form a positive hole transport layer of 40 nm in thickness. Further, the above heating boats, each carrying CBP and illustrated compound 1-1, were heated by applying an electric current to co-evaporate CBP and illustrated compound 1-1 onto the above-described positive hole transport layer at a deposition rate of 0.2 nm/sec and 0.012 nm/sec respectively to form a light-emitting layer of 40 nm in thickness.

The temperature of the substrate during deposition was room temperature. Further, the above heating boat carrying BCP was heated by applying an electric current to evaporate BCP onto the above-described light-emitting layer at a deposition rate of 0.1 nm/sec to form an electron transport layer of 10 nm in thickness. Furthermore, the above heating boat carrying Alq$_3$ was heated by applying an electric current to evaporate Alq$_3$ onto the above-described hole inhibition layer at a deposition rate of 0.1 nm/sec to form an electron transport layer of 40 nm in thickness. Temperature of the substrate during deposition was room temperature.

Subsequently, a cathode was prepared by evaporating lithium fluoride and aluminum onto the above sample with 0.5 nm and 110 nm in thickness respectively, to prepare organic EL element 1-1.

Preparation of Organic EL Elements 1-2 to 1-22

The organic EL elements 1-2 to 1-22 were prepared in the similar manner to the preparation of Organic EL element 1-1 except that the host compounds and light-emitting dopants were changed to those given in Table 1.

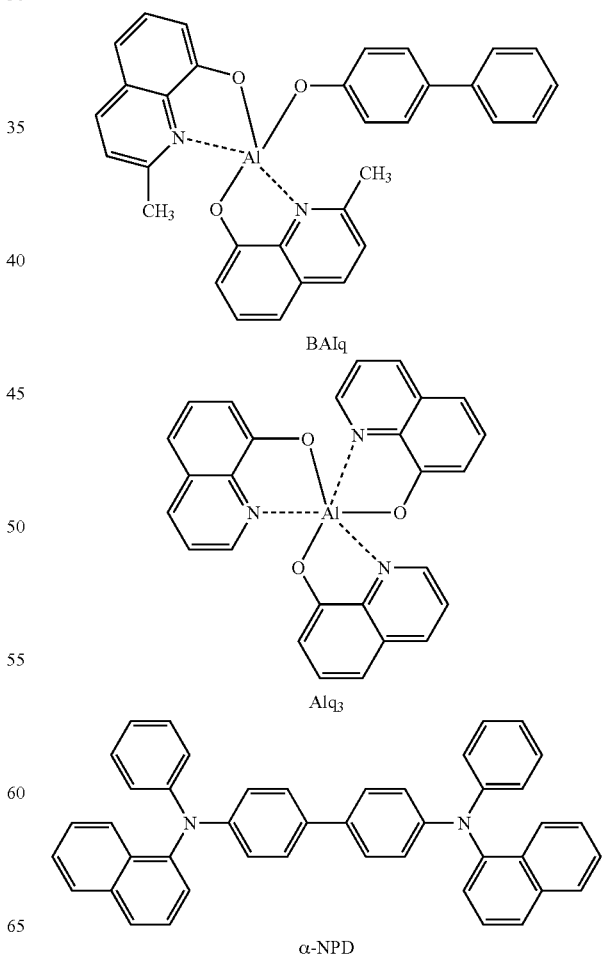

BAlq

Alq$_3$

α-NPD

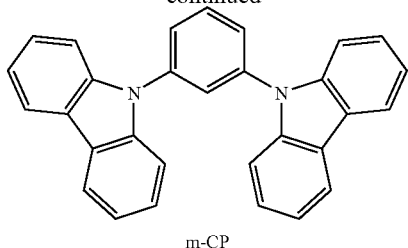

m-CP

<Evaluation of Organic EL Element>

Non-light emitting side of each organic EL element prepared above was covered) with a glass case. Using a glass substrate of 300 μm in thickness as a sealing substrate, the above glass case with the organic EL element being inside was put over the above-described cathode, and close contacted with the above-mentioned transparent substrate by applying an epoxy type light curable adhesive (LUX TRACK LC0629B; produced by TOAGOSEI CO., LTD.) as a sealant to the surroundings of the edges of the glass case. Then, the light curable adhesive was irradiated by UV light from the glass substrate side, to cure the adhesive, and then the organic EL element was sealed, to form a lighting apparatus as shown in FIG. 1 and FIG. 2, which was then subjected to an evaluation.

Figure 2:
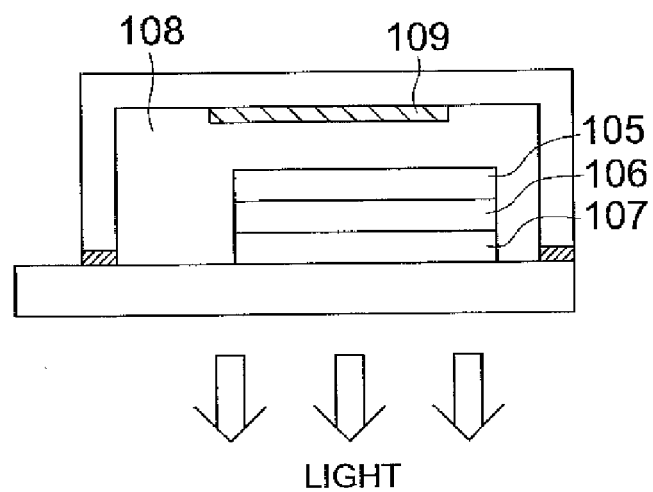
FIG. 2 is a schematic sectional view of the lighting apparatus.

FIG. 1 shows a schematic view of the lighting apparatus, and Organic EL element 101 is covered with Glass cover 102 (the sealing works were carried out in a glove box which was under nitrogen gas atmosphere (under at least 99.999% high purity nitrogen gas atmosphere) without Organic EL 101 being contacted with atmospheric gas.) FIG. 2 shows a schematic sectional view of the lighting apparatus, and in FIG. 2, 105 indicates a cathode, 106 indicates an organic EL layer, and 107 indicates a glass substrate equipped with a transparent electrode. Inside of Glass cover 102, Nitrogen gas 108 is fully charged and Moisture absorbing material 109 is provided.

(External Quantum Efficiency)

External quantum efficiency (%) of each of the prepared organic EL elements was determined with a constant current of 2.5 mA/cm² being supplied to each of the samples at 23° C. in a dry nitrogen gas atmosphere. A spectroradiometer CS-1000 (manufactured by Konica Minolta) was used for the measurement.

External quantum efficiency given in Table 1 was expressed by a relative value based on the external quantum efficiency of organic EL element 1-1 being 100.

(Emission Life)

A period in which brightness of an organic EL element, when driven at constant current of 2.5 mA/cm², decreased to half of the brightness immediately after the initiation of emission (initial brightness) was determined, and the period was defined as the half-life period (τ 0.5) and used as an index of the life of an organic EL element. A spectroradiometer CS-1000 (manufactured by Konica Minolta) was used for the measurement.

In Table 1, emission life was expressed by a relative value based on the emission life of organic EL element 1-1 being 100.

TABLE 1

| Organic EL element No. | Light-emitting dopant | Host compound | External quantum efficiency | Light emission life | Remarks |
|---|---|---|---|---|---|
| 1-1 | 1-1 | m-CP | 100 | 100 | Comp. |
| 1-2 | 1-2 | m-CP | 98 | 101 | Comp. |
| 1-3 | 1-5 | m-CP | 105 | 90 | Comp. |
| 1-4 | 1-1 | (1) | 130 | 140 | Inv. |
| 1-5 | 1-2 | (1) | 126 | 145 | Inv. |
| 1-6 | 1-5 | (1) | 122 | 134 | Inv. |
| 1-7 | 1-1 | (5) | 133 | 142 | Inv. |
| 1-8 | 1-2 | (5) | 124 | 143 | Inv. |
| 1-9 | 1-1 | (11) | 120 | 127 | Inv. |
| 1-10 | 1-2 | (11) | 116 | 132 | Inv. |
| 1-11 | 1-1 | (12) | 131 | 140 | Inv. |
| 1-12 | 1-2 | (12) | 125 | 141 | Inv. |
| 1-13 | 1-1 | (15) | 130 | 129 | Inv. |
| 1-14 | 1-1 | (19) | 119 | 121 | Inv. |
| 1-15 | 1-1 | (26) | 115 | 115 | Inv. |
| 1-16 | 1-1 | (32) | 133 | 130 | Inv. |
| 1-17 | 1-20 | (1) | 120 | 120 | Inv. |
| 1-18 | 1-20 | (5) | 119 | 115 | Inv. |
| 1-19 | 1-31 | (1) | 119 | 123 | Inv. |
| 1-20 | 1-31 | (5) | 121 | 120 | Inv. |
| 1-21 | 1-20 | m-CP | 99 | 98 | Comp. |
| 1-22 | 1-31 | m-CP | 97 | 93 | Comp. |

Comp.: Comparative example,
Inv.: Present invention

Tables 1 shows that the organic EL elements of the present invention achieved high external quantum efficiency and long life.

Example 2

Preparation of Organic EL Elements 2-1

A pattern was formed on a substrate composed of a glass plate of 100 mm×100 mm×1.1 mm and a 100 nm ITO (indium tin oxide) layer (NA45: manufactured by NH Technoglass Co., Ltd.) as an anode. Then the resulting transparent substrate, having the above ITO transparent electrode, was subjected to ultrasonic cleaning in iso-propylalcohol, dried with a dry nitrogen gas, and then subjected to UV-ozone cleaning for 5 minutes. Thus obtained transparent substrate was fixed to a substrate holder of a commercially available vacuum deposition apparatus. Further, 200 mg of α-NPD was placed in a first resistive heating molybdenum boat, 100 mg of CBP as a host compound was placed in a second resistive heating molybdenum boat, 200 mg of BAlq was placed in a third resistive heating molybdenum boat, 100 mg of Ir(ppy)₃ was placed in a fourth resistive heating molybdenum boat, and 200 mg of Alq₃ was placed in a fifth resistive heating molybdenum boat, and the resulting boats were fixed in the vacuum deposition apparatus.

After the pressure in the vacuum tank was reduced to 4×10⁻⁴ Pa, the above heating boat carrying α-NPD was heated by applying an electric current to evaporate α-NPD onto the transparent substrate at a deposition rate of 0.1 nm/sec to form a positive hole transport layer of 40 nm in thickness. Further, the above heating boat carrying CEP and Ir-1 each were heated by applying an electric current to co-evaporate CBP and Ir-1 each onto the positive hole transport layer at a deposition rate of 0.2 nm/sec and 0.012 nm/sec respectively to form an emission layer of 40 nm in thickness. The temperature of the substrate was at room temperature during deposition. Further, the above heating boats carrying BAlq was heated by applying an electric current to evaporate BAlq onto the above-described emission layer at a deposition rate of 0.1 nm/sec to form a hole inhibition layer of 10 nm in thickness. Further more, the above heating boats carrying Alq$_3$ was heated by applying an electric current to evaporate Alq$_3$ onto the above-described hole inhibition layer at a deposition rate of 0.1 nm/sec to form a electron transport layer of 40 nm in thickness. The temperature of the substrate during deposition was room temperature.

Subsequently, a cathode was prepared by evaporating lithium fluoride and aluminum onto the above sample with 0.5 nm and 110 nm in thickness respectively, to prepare organic EL element 2-1.

Preparation of Organic EL Elements 2-2 to 2-9

Organic EL Elements 2-2 to 2-9 were prepared in the same manner as organic EL element 2-1 in Example 1 except that the host compound were changed as described in Table 2.

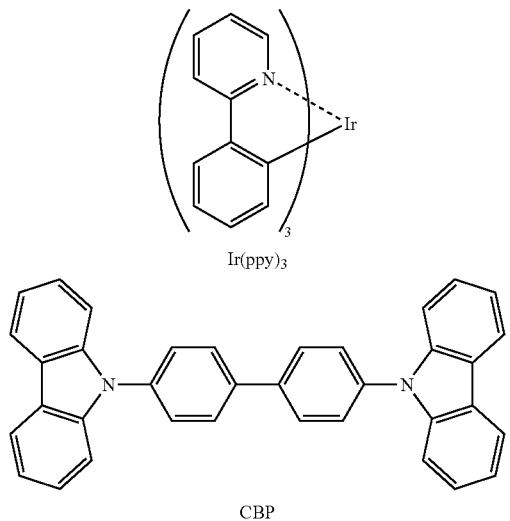

Ir(ppy)$_3$

CBP

These organic EL elements were sealed via the similar method to that of Example 1 and using a sealing can having the similar structure to that of Example 1, to produce flat lamps.

The prepared Organic EL elements 2-1 to 2-15 were evaluated similarly to Example 1 with the results shown in Table 2. External quantum efficiency and light emission life given in Table 2 were expressed by a relative value based on the external quantum efficiency and light emission life of Organic EL element 2-1 being 100.

TABLE 2

| Organic EL element No. | Host compound | External quantum efficiency | Light emission life | Remarks |
| --- | --- | --- | --- | --- |
| 2-1 | CBP | 100 | 100 | Comparative example |
| 2-2 | (1) | 115 | 126 | Present invention |
| 2-3 | (5) | 120 | 123 | Present invention |
| 2-4 | (11) | 121 | 127 | Present invention |
| 2-5 | (12) | 109 | 119 | Present invention |
| 2-6 | (15) | 110 | 112 | Present invention |
| 2-7 | (19) | 108 | 105 | Present invention |
| 2-8 | (26) | 118 | 115 | Present invention |
| 2-9 | (32) | 120 | 124 | Present invention |

Table 2 clearly shows that the organic EL elements of the present invention achieve high light emission efficiency, and longer light emission life, compared to comparative organic EL elements.

Example 3

Preparation of Organic EL Element 3-1

A pattern was formed on a substrate composed of a glass plate of 100 mm×100 mm×1.1 mm and a 100 nm ITO (indium tin oxide) layer (NA45: manufactured by NH Technoglass Co., Ltd.) as an anode. Then the resulting transparent substrate, having the above ITO transparent electrode, was subjected to ultrasonic cleaning in iso-propylalcohol, dried with a dry nitrogen gas, and then subjected to UV-ozone cleaning for 5 minutes. Thus obtained transparent substrate was fixed to a substrate holder of a commercially available vacuum deposition apparatus. Further, 200 mg of α-NPD was placed in a first resistive heating molybdenum boat, 100 mg of m-CP, as an electron blocking compound, was placed in a second resistive heating molybdenum boat, 200 mg of CBP, as a host compound was placed in a third resistive heating molybdenum boat, 200 mg of BAlq was placed in a fourth resistive heating molybdenum boat, 100 mg of Light emitting dopant 1-1 was placed in a fifth resistive heating molybdenum boat, and 200 mg of Alq$_3$ was placed in a sixth resistive heating molybdenum boat, and the resulting boats were fixed in the vacuum deposition apparatus.

After the pressure in the vacuum tank was reduced to 4×10$^{-4}$ Pa, the above heating boat carrying α-NPD was heated by applying an electric current to evaporate α-NPD onto the transparent substrate at a deposition rate of 0.1 nm/sec to form a positive hole transport layer of 40 nm in thickness. Further, the above heating boat carrying m-CP was heated by applying an electric current to evaporate m-CP onto the positive hole transport layer at a deposition rate of 0.1 nm/sec to form an electron inhibition layer of 10 nm in thickness. Further, the above heating boats, each carrying CBP and Light emitting dopant 1-1, were heated by applying an electric current to co-evaporate CBP and Light emitting dopant 1-1 onto the above-described positive hole transport layer at a deposition rate of 0.2 nm/sec and 0.012 nm/sec respectively to form a light-emitting layer of 40 nm in thickness. The temperature of the substrate during deposition was room temperature. Further, the above heating boat carrying BAlq was heated by applying an electric current to evaporate BAlq onto the above-described light-emitting layer at a deposition rate of 0.1 nm/sec to form a positive hole inhibition layer of 10 nm in thickness. Furthermore, the above heating boat carrying Alq$_3$ was heated by applying an electric current to evaporate Alq$_3$ onto the above-described positive hole inhibition layer at a deposition rate of 0.1 nm/sec to form an electron transport layer of 40 nm in thickness. Temperature of the substrate during deposition was room temperature.

Subsequently, a cathode was prepared by evaporating lithium fluoride and aluminum onto the above sample with 0.5 nm and 110 nm in thickness respectively, to prepare organic EL element 3-1.

Preparation of Organic EL Element 3-2 to 3-9

Organic EL elements 3-2 to 3-9 were prepared in the same manner as in preparation of Organic EL Element 3-1 except that CBP, which was employed as a host compound in a light-emitting layer, was changed to those compounds given in Table 3, and M-CP, which was employed in an electron inhibition layer, was changed to those compounds given in Table 3.

The prepared Organic EL elements 3-1 to 3-9 were evaluated similarly to Example 1, with the results shown in Table 3. External quantum efficiency and light emission life given in Table 3 were expressed by a relative value based on the external quantum efficiency and light emission life of organic EL element 3-1 being 100.

TABLE 3

| Organic EL element No. | Electron inhibition layer | Host compound | External quantum efficiency | Light emission life | Remarks |
| --- | --- | --- | --- | --- | --- |
| 3-1 | m-CP | CBP | 100 | 100 | Comparative example |
| 3-2 | (1) | (1) | 128 | 131 | Present invention |
| 3-3 | (5) | (5) | 127 | 127 | Present invention |
| 3-4 | (11) | (11) | 126 | 124 | Present invention |
| 3-5 | (12) | (12) | 119 | 123 | Present invention |
| 3-6 | (5) | (1) | 130 | 132 | Present invention |
| 3-7 | (11) | (1) | 110 | 119 | Present invention |
| 3-8 | (12) | (1) | 113 | 115 | Present invention |
| 3-9 | (1) | m-CP | 105 | 108 | Present invention |

Table 3 clearly shows that the organic EL elements of the present invention achieve high light emission efficiency, and longer light emission life, compared to comparative organic EL elements.

Example 4

Preparation of Organic EL Element 4-1

A pattern was formed on a substrate composed of a glass plate of 100 mm×100 mm×1.1 mm and a 100 nm ITO (indium tin oxide) layer (NA45: manufactured by NH Technoglass Co., Ltd.) as an anode. Then the resulting transparent substrate, having the above ITO transparent electrode, was subjected to ultrasonic cleaning in iso-propylalcohol, dried with a dry nitrogen gas, and then subjected to UV-ozone cleaning for 5 minutes. Thus obtained transparent substrate was fixed to a substrate holder of a commercially available vacuum deposition apparatus. Further, 200 mg of α-NPD was placed in a first resistive heating molybdenum boat, 200 mg of m-CP, as an host compound, was placed in a second resistive heating molybdenum boat, 200 mg of BAlq was placed in a third resistive heating molybdenum boat, 100 mg of light emitting dopant was placed in a fourth resistive heating molybdenum boat, 200 mg of Alq$_3$ was placed in a fifth resistive heating molybdenum boat, and the resulting boats were fixed in the vacuum deposition apparatus.

After the pressure in the vacuum tank was reduced to $4 \times 10^{-4}$ Pa, the above heating boat carrying α-NPD was heated by applying an electric current to evaporate α-NPD onto the transparent substrate at a deposition rate of 0.1 nm/sec to form a positive hole transport layer of 40 nm in thickness. Further, the above heating boat carrying m-CP was heated by applying an electric current to evaporate m-CP onto the positive hole transport layer at a deposition rate of 0.1 nm/sec to form an electron inhibition layer of 10 nm in thickness. Further, the above heating boats, each carrying m-CP and Light emitting dopant 1-1, were heated by applying an electric current to co-evaporate m-CP and Light emitting dopant 1-1 onto the above-described positive hole transport layer at a deposition rate of 0.2 nm/sec and 0.012 nm/sec respectively to form a light-emitting layer of 40 nm in thickness. The temperature of the substrate during deposition was room temperature. Further, the above heating boat carrying BAlq was heated by applying an electric current to evaporate BAlq onto the above-described light-emitting layer at a deposition rate of 0.1 nm/sec to form a positive hole inhibition layer of 10 nm in thickness. Furthermore, the above heating boat carrying Alq$_3$ was heated by applying an electric current to evaporate Alq$_3$ onto the above-described positive hole inhibition layer at a deposition rate of 0.1 nm/sec to form an electron transport layer of 40 nm in thickness. Temperature of the substrate during deposition was room temperature.

Subsequently, a cathode was prepared by evaporating lithium fluoride and aluminum onto the above sample with 0.5 nm and 110 nm in thickness respectively, to prepare Organic EL element 4-1.

Preparation of Organic EL Element 4-2 to 4-5

Organic EL elements 4-2 to 4-5 were prepared in the same manner as in preparation of Organic EL Element 4-1 except that m-CP, which was employed as a host compound in a light-emitting layer, was changed to those compounds given in Table 4, and BAlq, which was employed in an positive hole inhibition layer, was changed to those compounds given in Table 4.

The prepared Organic EL elements 4-1 to 4-5 were evaluated similarly to Example 1, with the results shown in Table 4. External quantum efficiency and light emission life given in Table 4 were expressed by a relative value based on the external quantum efficiency and light emission life of Organic EL element 4-1 being 100.

TABLE 4

| Organic EL element No. | Host compound | Positive hole inhibition layer | External quantum efficiency | Light emission life | Remarks |
| --- | --- | --- | --- | --- | --- |
| 4-1 | m-CP | Balq | 100 | 100 | Comparative example |
| 4-2 | (1) | (1) | 120 | 105 | Present invention |
| 4-3 | (11) | (11) | 118 | 106 | Present invention |
| 4-4 | (1) | (11) | 123 | 110 | Present invention |
| 4-5 | m-CP | (11) | 110 | 103 | Present invention |

Table 4 clearly shows that the organic EL elements of the present invention can achieve high light emission efficiency, and longer light emission life, compared to comparative organic EL elements.

Example 5

A pattern of an electrode of the transparent electrode substrate of Example 1 was formed having 20 mm×20 mm in size, and on which a film of α-NPD, as a positive hole injection/transport layer, was formed to 50 nm in thickness. Further, the above-described heating boat carrying Illustrated compound 1-1, a boat carrying Light emitting dopant 1-1, and a boat carrying Ir-9 were heated by applying an electric current individually to evaporate them onto the above electrode, by controlling deposition rates of Illustrated compound 1-1, Light emitting dopant 1-1, and Ir-9 to be 100:5:0.6, to form a light-emitting layer of 30 nm in thickness.

Next, an electron transport layer was provided by foaming a film of BAlq to 10 nm in thickness. Further, an electron injection layer was provided by foaming a film of $Alq_3$ to 40 nm in thickness.

Subsequently, the vacuum chamber was opened, and a stainless-steel mask, having square holes with almost the same shape as the transparent electrode, was provided on the electron injection layer, and then a lithium fluoride was evaporated to form a layer as a cathode buffer layer with 0.5 nm in thickness, and aluminum was evaporated to form a layer as a cathode with 150 nm in thickness.

The above element was sealed using the similar method and a sealing can having the similar structure to those of Example 1, to produce a flat lamp.

The above flat lamp emitted a nearly white light by applying an electric current to prove that the aforesaid lamp is usable as a lighting apparatus. It was found that other flat lamps, in which the host compound was replace by other host compounds of the present invention, also similarly emitted white light.

What is claimed is:

1. An organic electroluminescence element material represented by Formula (1),

Formula (1):

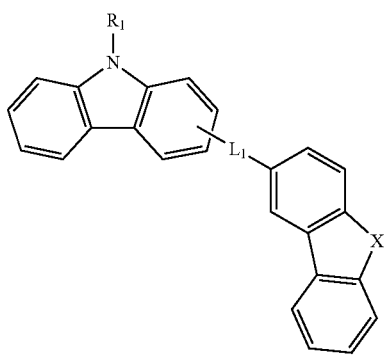

wherein
$R_1$ represents a hydrogen atom, an aliphatic group, an aromatic hydrocarbon cyclic group, or a heterocyclic group;

$L_1$ represents a phenylene group or a simple bond;

X represents O or S; and the compound represented by Formula (1) may have a substituent at another position, the substituent selected from the group consisting of an alkyl group, a cycloalkyl group, an alkenyl group, an alkynyl group, an aromatic hydrocarbon ring group, an aromatic heterocyclic group, a heterocyclic group, an alkoxy group, a cycloalkoxy group, an aryloxy group, an alkylthio group, a cycloalkylthio group, an arylthio group, an alkylthio group, a cycloalkylthio group, an arylthio group, an alkoxycarbonyl group, an aryloxycarbonyl group, a sulfamoyl group, an acyl group, an acyloxy group, an amido group, a carbamoyl group, an ureido group, a sulfinyl group, an alkylsulfonyl group, an arylsulfonyl group, an amino group, a halogen atom, a fluorinated hydrocarbon group, a cyano group, and a silyl group.

2. An organic electroluminescence element material of claim 1, wherein $L_1$ in Formula (1) represents a simple bond.

3. An organic electroluminescence element material of claim 1, wherein X in Formula (1) represents O.

4. An organic electroluminescence element incorporating at least a light-emitting layer which is sandwiched between an anode and a cathode, wherein the organic electroluminescence element incorporates the organic electroluminescence element material of claim 1.

5. An organic electroluminescence element of claim 4, wherein the light-emitting layer contains a phosphorescent emission dopant.

6. An organic electroluminescence element of claim 5, wherein the 0-0 band of the above phosphorescent emission dopant is 485 nm or less.

7. An organic electroluminescence element of claim 4 incorporating the organic electroluminescence element material in the light-emitting layer.

8. An organic electroluminescence element of claim 4, wherein the organic electroluminescence element has a hole block layer as a constituting layer, and the hole block layer incorporates the organic electroluminescence element material.

9. An organic electroluminescence element of claim 4, wherein the organic electroluminescence element emits white light.

10. A display device, wherein the display device is provided with an organic electroluminescence element of claim 4.

11. A lighting apparatus, wherein the lighting apparatus is provided with an organic electroluminescence element of claim 4.

12. A display device, wherein the display device has the lighting apparatus of claim 11, and a liquid crystal element as a display means.

13. An organic electroluminescence element material represented by Formula (2),

Formula (2):

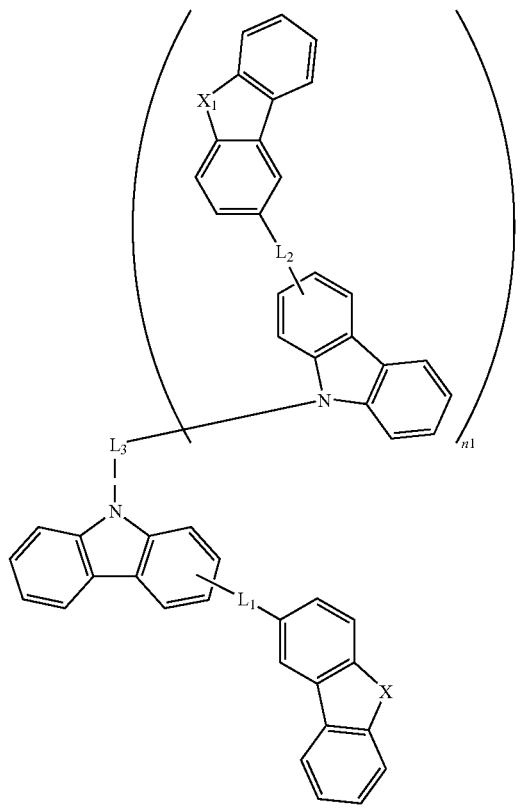

wherein, $L_1$ and $L_2$ represent a linking group or a simple bond; $L_3$ represents a linking group;

X represents O or S;

$X_1$ represents O, S, or NRa;

n1 represents an integer of 1 to 5;

Ra represents a hydrogen atom, an aliphatic group, an aromatic hydrocarbon cyclic group, or a heterocyclic group; and the compound represented by Formula (2) may have a substituent at another position.

14. An organic electroluminescence element material of claim 13, wherein $L_3$ of Formula (2) represents a bivalent linking group derived from an aromatic hydrocarbon cyclic group, or a heterocyclic group.

15. An organic electroluminescence element material represented by Formula (3),

Formula (3):

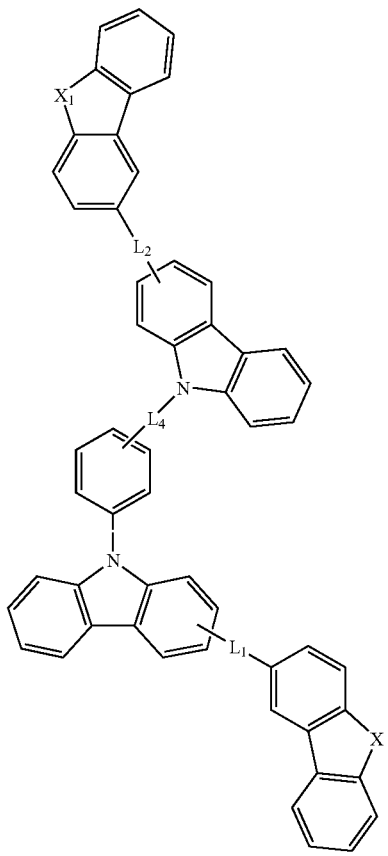

wherein, $L_1$, $L_2$, and $L_4$ represent a linking group or a simple bond;

X represents O or S;

$X_1$ represents O, S, or NRa;

Ra represents a hydrogen atom, an aliphatic group, an aromatic hydrocarbon cyclic group, or a heterocyclic group; and the compound represented by Formula (3) may have a substituent at another position.

16. An organic electroluminescence element material represented by Formula (4),

Formula (4):

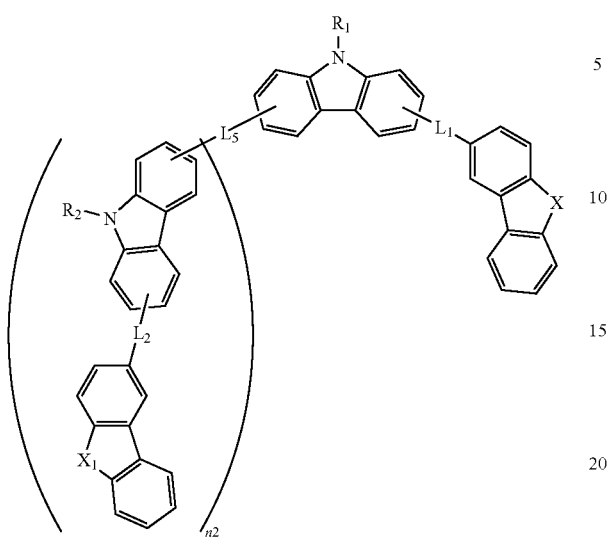

wherein
$R_1$ and $R_2$ represent a hydrogen atom, an aliphatic group, an aromatic hydrocarbon cyclic group, or a heterocyclic group;
$L_1$ and $L_2$ represent a linking group or a simple bond;
$L_5$ represents a linking group;
X represents O or S;
$X_1$ represents O, S, or NRa;
n2 represents an integer of 1 to 5;
Ra represents a hydrogen atom, an aliphatic group, an aromatic hydrocarbon cyclic group, or a heterocyclic group; and
the compound represented by Formula (3) may have a substituent at another position.

17. An organic electroluminescence element material of claim 16, wherein $L_5$ of Formula (4) represents a bivalent linking group derived from an aromatic hydrocarbon cyclic group, or a heterocyclic group.

18. An organic electroluminescence element material represented by Formula (5),

Formula (5):

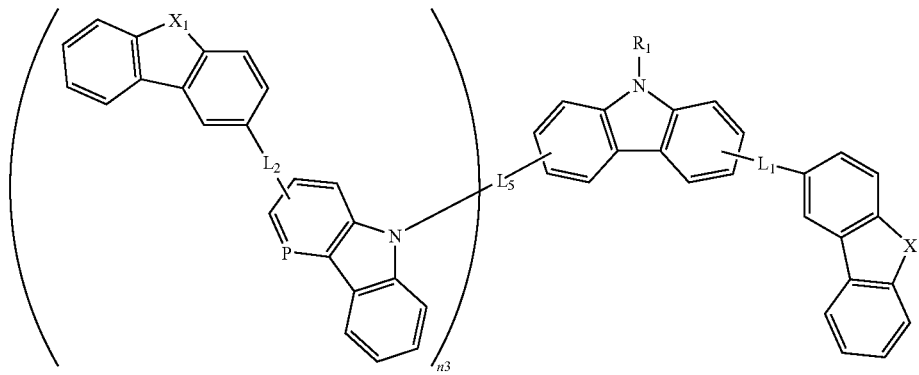

wherein
$R_1$ represents a hydrogen atom, an aliphatic group, an aromatic hydrocarbon cyclic group, or a heterocyclic group;
$L_1$ and $L_2$ represent a linking group or a simple bond;
$L_6$ represents a linking group;
X represents O or S;
$X_1$ represents O, S, or NRa;
n3 represents an integer of 1 to 5;
Ra represents a hydrogen atom, an aliphatic group, an aromatic hydrocarbon cyclic group, or a heterocyclic group; and
the compound represented by Formula (3) may have a substituent at another position.

19. An organic electroluminescence element material of claim 18, wherein $L_6$ of the above Formula (5) represents a bivalent linking group derived from an aromatic hydrocarbon cyclic group, or a heterocyclic group.

20. An organic electroluminescence element comprising:
an anode and a cathode;

a light-emitting layer sandwiched between the anode and the cathode;

an electron inhibition layer between the anode and the cathode; and an organic electroluminescence element material incorporated in the electron inhibition layer, the organic electroluminescence element material represented by Formula (1), Formula (1):

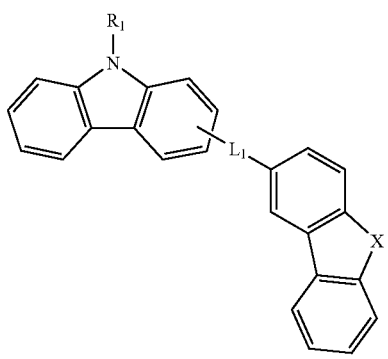

wherein
$R_1$ represents a hydrogen atom, an aliphatic group, an aromatic hydrocarbon cyclic group, or a heterocyclic group;
$L_1$ represents a linking group or a simple bond;
X represents O or S; and
the compound represented by Formula (1) may have a substituent at another position, the substituent selected from the group consisting of an alkyl group, a cycloalkyl group, an alkenyl group, an alkynyl group, an aromatic hydrocarbon ring group, an aromatic heterocyclic group, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amido group, a carbamoyl group, an ureido group, a sulfinyl group, an alkylsulfonyl group, an arylsulfonyl group, an amino group, a halogen atom, a fluorinated hydrocarbon group, a cyano group, and a silyl group.

* * * * *